(12) United States Patent
Cochran et al.

(10) Patent No.: US 12,409,125 B2
(45) Date of Patent: *Sep. 9, 2025

(54) SHAMPOO COMPOSITIONS CONTAINING A SULFATE-FREE SURFACTANT SYSTEM AND SCLEROTIUM GUM THICKENER

(71) Applicant: The Procter & Gamble Company, Cincinnati, OH (US)

(72) Inventors: Brooke Michele Cochran, Cincinnati, OH (US); Mark Anthony Brown, Union, KY (US); Jean Jianqun Zhao, Cincinnati, OH (US); Lauren Elizabeth Ballhaus, Williamsburg, OH (US); Nicole Marie Mazzei, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,697

(22) Filed: May 6, 2022

(65) Prior Publication Data

US 2022/0378684 A1 Dec. 1, 2022

Related U.S. Application Data

(60) Provisional application No. 63/276,108, filed on Nov. 5, 2021, provisional application No. 63/188,517, filed on May 14, 2021.

(51) Int. Cl.
| | |
|---|---|
| *A61K 8/60* | (2006.01) |
| *A61K 8/19* | (2006.01) |
| *A61K 8/368* | (2006.01) |
| *A61K 8/49* | (2006.01) |
| *A61K 8/73* | (2006.01) |
| *A61K 8/92* | (2006.01) |
| *A61K 8/9789* | (2017.01) |
| *A61Q 5/02* | (2006.01) |
| *A61Q 17/00* | (2006.01) |

(52) U.S. Cl.
CPC .............. *A61K 8/604* (2013.01); *A61K 8/19* (2013.01); *A61K 8/368* (2013.01); *A61K 8/4926* (2013.01); *A61K 8/4946* (2013.01); *A61K 8/4953* (2013.01); *A61K 8/73* (2013.01); *A61K 8/737* (2013.01); *A61K 8/922* (2013.01); *A61K 8/9789* (2017.08); *A61Q 5/02* (2013.01); *A61Q 17/005* (2013.01); *A61K 2800/33* (2013.01); *A61K 2800/5426* (2013.01)

(58) Field of Classification Search
CPC .......... A61K 8/604; A61K 8/19; A61K 8/368; A61K 8/4926; A61K 8/4946; A61K 8/4953; A61K 8/73; A61K 8/737; A61K 8/922; A61K 8/9789; A61K 8/42; A61K 8/44; A61K 8/466; A61K 8/731; A61K 8/732; A61K 8/8158; A61K 2800/30; A61K 2800/596; A61K 2800/33; A61K 2800/5426; A61K 2800/52; A61Q 5/02; A61Q 5/12; A61Q 17/005
See application file for complete search history.

(56) References Cited

U.S. PATENT DOCUMENTS

| | | | |
|---|---|---|---|
| 1,489,388 A | 4/1924 | Glenn | |
| 1,600,340 A | 9/1926 | Hoffman | |
| 1,612,255 A | 12/1926 | William | |
| 2,438,091 A | 3/1948 | Lynch | |
| 2,528,378 A | 10/1950 | Mannheimer | |
| 2,658,072 A | 11/1953 | Milton | |
| 2,809,971 A | 10/1957 | Bernstein et al. | |
| 2,879,231 A | 3/1959 | Marshall | |
| 3,219,656 A | 11/1965 | Boettner | |
| 3,236,733 A | 2/1966 | Karsten et al. | |
| 3,373,208 A | 3/1968 | Blumenthal | |
| 3,636,113 A | 1/1972 | Hall | |
| 3,709,437 A | 1/1973 | Wright | |
| 3,716,498 A | 2/1973 | Hall | |
| 3,753,196 A | 8/1973 | Kurtz et al. | |
| 3,761,418 A | 9/1973 | Parran | |
| 3,792,068 A | 2/1974 | Luedders et al. | |
| 3,887,692 A | 6/1975 | Gilman | |
| 3,904,741 A | 9/1975 | Jones et al. | |
| 3,950,532 A | 4/1976 | Bouillon et al. | |
| 3,959,160 A | 5/1976 | Horsler et al. | |

(Continued)

FOREIGN PATENT DOCUMENTS

| | | |
|---|---|---|
| BE | 825146 A | 8/1975 |
| BR | 199400875 A | 5/1996 |

(Continued)

OTHER PUBLICATIONS

"Anti-Dandruff Shampoo", Mintel Database, Record No. 752198, dated Aug. 2007; pp. 1-3.
"Dandruff Control Shampoo", Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.

(Continued)

*Primary Examiner* — Benjamin J Packard
*Assistant Examiner* — Lucy M Tien
(74) *Attorney, Agent, or Firm* — Abbey A. Lopez; John G. Powell

(57) ABSTRACT

A stable shampoo composition containing a surfactant system that is substantially free of sulfated surfactants. The shampoo composition also contains an anionic surfactant, an amphoteric surfactant, a cationic polymer and a sclerotium gum thickener. The shampoo composition has a consumer-preferred viscosity of greater than 2500 cP, a pH greater than 5.5 and lacks in-situ coacervate.

16 Claims, 6 Drawing Sheets

(56) References Cited

U.S. PATENT DOCUMENTS

| | | |
|---|---|---|
| 4,049,792 A | 9/1977 | Elsnau |
| 4,089,945 A | 5/1978 | Brinkman et al. |
| 4,120,948 A | 10/1978 | Shelton |
| 4,137,180 A | 1/1979 | Naik |
| 4,237,155 A | 12/1980 | Kardouche |
| 4,309,119 A | 1/1982 | Wittersheim |
| 4,323,683 A | 4/1982 | Bolich, Jr. et al. |
| 4,329,334 A | 5/1982 | Su et al. |
| 4,345,080 A | 8/1982 | Bolich |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,726,945 A | 2/1988 | Patel |
| 4,732,696 A | 3/1988 | Urfer |
| 4,839,166 A | 6/1989 | Grollier et al. |
| 4,854,333 A | 8/1989 | Inman et al. |
| 4,867,971 A | 9/1989 | Ryan et al. |
| 4,931,274 A | 6/1990 | Barabino et al. |
| 4,973,416 A | 11/1990 | Kennedy |
| 4,985,238 A | 1/1991 | Tanner et al. |
| 4,997,641 A | 3/1991 | Hartnett |
| 5,019,375 A | 5/1991 | Tanner et al. |
| 5,093,112 A | 3/1992 | Birtwistle et al. |
| 5,104,646 A | 4/1992 | Bolich, Jr. |
| 5,106,609 A | 4/1992 | Bolich, Jr. |
| 5,135,747 A | 8/1992 | Faryniarz et al. |
| 5,156,834 A | 10/1992 | Beckmeyer et al. |
| 5,294,644 A | 3/1994 | Login et al. |
| 5,296,157 A | 3/1994 | Macgilp et al. |
| 5,296,622 A | 3/1994 | Uphues |
| 5,298,640 A | 3/1994 | Callaghan et al. |
| 5,332,569 A | 7/1994 | Wood et al. |
| 5,364,031 A | 11/1994 | Taniguchi et al. |
| 5,374,421 A | 12/1994 | Tashiro |
| 5,374,614 A | 12/1994 | Behan et al. |
| 5,409,695 A | 4/1995 | Abrutyn et al. |
| 5,415,810 A | 5/1995 | Lee et al. |
| 5,417,965 A | 5/1995 | Janchitraponvej et al. |
| 5,429,816 A | 7/1995 | Hofrichter et al. |
| 5,439,682 A | 8/1995 | Wivell |
| 5,441,659 A | 8/1995 | Minor |
| 5,486,303 A | 1/1996 | Capeci |
| 5,489,392 A | 2/1996 | Capeci |
| 5,496,488 A | 3/1996 | Kacher et al. |
| 5,516,448 A | 5/1996 | Capeci |
| 5,536,493 A | 7/1996 | Dubief |
| 5,554,588 A | 9/1996 | Behan et al. |
| 5,560,918 A | 10/1996 | Wivell |
| 5,565,422 A | 10/1996 | Del Greco |
| 5,569,645 A | 10/1996 | Dinniwell |
| 5,574,005 A | 11/1996 | Welch |
| 5,576,282 A | 11/1996 | Miracle |
| 5,578,298 A | 11/1996 | Berthiaume |
| 5,595,967 A | 1/1997 | Miracle |
| 5,597,936 A | 1/1997 | Perkins |
| 5,599,549 A | 2/1997 | Wivell |
| 5,624,666 A | 4/1997 | Coffindaffer et al. |
| 5,635,469 A | 6/1997 | Fowler et al. |
| 5,665,267 A | 9/1997 | Dowell et al. |
| 5,691,297 A | 11/1997 | Nassano |
| 5,714,137 A | 2/1998 | Trinh |
| 5,747,436 A | 5/1998 | Patel |
| 5,776,444 A | 7/1998 | Birtwistle et al. |
| 5,800,897 A | 9/1998 | Sharma |
| 5,816,446 A | 10/1998 | Steindorf et al. |
| 5,830,440 A | 11/1998 | Sturla et al. |
| 5,853,618 A | 12/1998 | Barker |
| 5,879,584 A | 3/1999 | Bianchetti |
| 5,891,424 A | 4/1999 | Bretzler et al. |
| 5,902,225 A | 5/1999 | Monson |
| 5,925,603 A | 7/1999 | D'Angelo |
| 5,942,217 A | 8/1999 | Woo et al. |
| 5,976,514 A | 11/1999 | Guskey et al. |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,139,828 A | 10/2000 | Mccullough |
| 6,153,567 A | 11/2000 | Hughes |
| 6,153,569 A | 11/2000 | Halloran |
| 6,162,834 A | 12/2000 | Sebillotte-Arnaud et al. |
| 6,180,121 B1 | 1/2001 | Guenin et al. |
| 6,225,464 B1 | 5/2001 | Hiler, II |
| 6,231,844 B1 | 5/2001 | Nambu |
| 6,232,302 B1 | 5/2001 | Alberico et al. |
| 6,248,135 B1 | 6/2001 | Trinh et al. |
| 6,268,431 B1 | 7/2001 | Snyder et al. |
| 6,284,225 B1 | 9/2001 | Bhatt |
| 6,329,331 B1 | 12/2001 | Aronson |
| 6,335,312 B1 | 1/2002 | Coffindaffer et al. |
| 6,352,688 B1 | 3/2002 | Scavone et al. |
| 6,386,392 B1 | 5/2002 | Argentieri |
| 6,413,920 B1 | 7/2002 | Bettiol |
| 6,423,305 B1 | 7/2002 | Cauwet-Martin et al. |
| 6,436,442 B1 | 8/2002 | Woo et al. |
| 6,451,300 B1 | 9/2002 | Dunlop et al. |
| 6,488,943 B1 | 12/2002 | Beerse et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,656,923 B1 | 12/2003 | Trinh |
| 6,660,288 B1 | 12/2003 | Behan et al. |
| 6,679,324 B2 | 1/2004 | Den Boer et al. |
| 6,716,455 B2 | 4/2004 | Birkel |
| 6,716,805 B1 | 4/2004 | Sherry |
| 6,740,713 B1 | 5/2004 | Busch et al. |
| 6,743,760 B1 | 6/2004 | Hardy et al. |
| 6,764,986 B1 | 7/2004 | Busch et al. |
| 6,767,507 B1 | 7/2004 | Woo et al. |
| 6,794,356 B2 | 9/2004 | Turner |
| 6,814,088 B2 | 11/2004 | Barnabas et al. |
| 6,827,795 B1 | 12/2004 | Kasturi et al. |
| 6,869,923 B1 | 3/2005 | Cunningham |
| 6,897,253 B2 | 5/2005 | Schmucker-castner |
| 6,908,889 B2 | 6/2005 | Niemiec et al. |
| 6,930,078 B2 | 8/2005 | Wells |
| 6,992,054 B2 | 1/2006 | Lee et al. |
| 7,018,978 B2 | 3/2006 | Miracle et al. |
| 7,030,068 B2 | 4/2006 | Clare et al. |
| 7,100,767 B2 | 9/2006 | Chomik et al. |
| 7,151,079 B2 | 12/2006 | Fack et al. |
| 7,172,099 B2 | 2/2007 | Hoefte |
| 7,202,198 B2 | 4/2007 | Gordon et al. |
| 7,217,752 B2 | 5/2007 | Schmucker-Castner et al. |
| 7,220,408 B2 | 5/2007 | Decoster et al. |
| 7,223,361 B2 | 5/2007 | Kvietok |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,598,213 B2 | 10/2009 | Geary et al. |
| 7,659,233 B2 | 2/2010 | Conopco |
| 7,666,825 B2 | 2/2010 | Wagner et al. |
| 7,820,609 B2 | 10/2010 | Soffin et al. |
| 7,829,514 B2 | 11/2010 | Paul et al. |
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,058,500 B2 | 11/2011 | Sojka et al. |
| 8,084,407 B2 | 12/2011 | Soffin et al. |

(56) References Cited

U.S. PATENT DOCUMENTS

| | | |
|---|---|---|
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,357,359 B2 | 1/2013 | Woo et al. |
| 8,361,450 B2 | 1/2013 | Johnson et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,539,631 B2 | 9/2013 | Catalfamo et al. |
| 8,574,561 B1 | 11/2013 | Patel et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,511,007 B2 | 12/2016 | Frantz et al. |
| 9,512,275 B2 | 12/2016 | Wagner |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,949,911 B2 | 4/2018 | Cetti |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song |
| 10,441,519 B2 | 10/2019 | Zhao |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 11,116,703 B2 | 9/2021 | Song et al. |
| 11,116,704 B2 | 9/2021 | Song et al. |
| 11,129,775 B2 | 9/2021 | Song et al. |
| 11,334,694 B2 | 5/2022 | Cetti et al. |
| 11,334,695 B2 | 5/2022 | Cetti et al. |
| 11,904,036 B2 | 2/2024 | Song |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0202952 A1 | 10/2003 | Wells et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0064117 A1 | 4/2004 | Hammons |
| 2004/0131660 A1 | 7/2004 | Lange et al. |
| 2004/0144863 A1 | 7/2004 | Kendrick |
| 2004/0151793 A1 | 8/2004 | Paspaleeva-kuhn et al. |
| 2004/0157754 A1 | 8/2004 | Geary et al. |
| 2004/0229963 A1 | 11/2004 | Stephane |
| 2004/0234484 A1 | 11/2004 | Peffly |
| 2004/0235689 A1 | 11/2004 | Sakai et al. |
| 2005/0003975 A1 | 1/2005 | Browne et al. |
| 2005/0003980 A1 | 1/2005 | Baker |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0192207 A1 | 9/2005 | Morgan, III et al. |
| 2005/0201967 A1 | 9/2005 | Albrecht et al. |
| 2005/0202984 A1 | 9/2005 | Schwartz et al. |
| 2005/0208106 A1 | 9/2005 | Lange et al. |
| 2005/0227902 A1 | 10/2005 | Erazo-majewicz et al. |
| 2005/0233929 A1 | 10/2005 | Queen |
| 2005/0245407 A1 | 11/2005 | Ishihara |
| 2005/0276831 A1 | 12/2005 | Dihora |
| 2006/0002880 A1 | 1/2006 | Peffly |
| 2006/0005333 A1 | 1/2006 | Catalfamo et al. |
| 2006/0009337 A1 | 1/2006 | Smith |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0084589 A1 | 4/2006 | Vlad et al. |
| 2006/0090777 A1 | 5/2006 | Hecht et al. |
| 2006/0094610 A1 | 5/2006 | Yamato et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0166857 A1 | 7/2006 | Surburg et al. |

(56) References Cited

U.S. PATENT DOCUMENTS

| | | |
|---|---|---|
| 2006/0171911 A1 | 8/2006 | Schwartz et al. |
| 2006/0182703 A1 | 8/2006 | Arisz |
| 2006/0183662 A1 | 8/2006 | Crotty |
| 2006/0210139 A1 | 9/2006 | Carroll |
| 2006/0229227 A1 | 10/2006 | Goldman |
| 2006/0252662 A1 | 11/2006 | Soffin |
| 2006/0263319 A1 | 11/2006 | Fan et al. |
| 2006/0269503 A1 | 11/2006 | Yamazaki |
| 2006/0276357 A1 | 12/2006 | Smith et al. |
| 2006/0292104 A1 | 12/2006 | Guskey |
| 2007/0003499 A1 | 1/2007 | Shen et al. |
| 2007/0020263 A1 | 1/2007 | Shitara et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0275866 A1 | 11/2007 | Dykstra |
| 2007/0292380 A1 | 12/2007 | Staudigel |
| 2007/0298994 A1 | 12/2007 | Finke et al. |
| 2008/0003245 A1 | 1/2008 | Kroepke et al. |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |
| 2008/0176780 A1 | 7/2008 | Warr |
| 2008/0194454 A1 | 8/2008 | Morgan |
| 2008/0206179 A1 | 8/2008 | Peffly et al. |
| 2008/0229512 A1 | 9/2008 | Syed et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0005280 A1 | 1/2009 | Woo et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0240223 A1 | 9/2009 | Warren |
| 2009/0246236 A1 | 10/2009 | Kitko |
| 2009/0312223 A1 | 12/2009 | Yang et al. |
| 2009/0312224 A1 | 12/2009 | Yang et al. |
| 2009/0324505 A1 | 12/2009 | Seidling |
| 2010/0000116 A1 | 1/2010 | Aouad et al. |
| 2010/0001116 A1 | 1/2010 | Johnson |
| 2010/0009285 A1 | 1/2010 | Daems et al. |
| 2010/0061946 A1 | 3/2010 | Scherner et al. |
| 2010/0087357 A1 | 4/2010 | Morgan, III et al. |
| 2010/0152083 A1 | 6/2010 | Velazquez |
| 2010/0168251 A1 | 7/2010 | Warr et al. |
| 2010/0183539 A1 | 7/2010 | Bernhardt |
| 2010/0215775 A1 | 8/2010 | Schmaus et al. |
| 2010/0287710 A1 | 11/2010 | Denutte et al. |
| 2010/0310644 A1 | 12/2010 | Liebmann |
| 2010/0322878 A1 | 12/2010 | Stella et al. |
| 2011/0008267 A1 | 1/2011 | Arkin et al. |
| 2011/0023266 A1 | 2/2011 | Gross et al. |
| 2011/0098209 A1 | 4/2011 | Smets et al. |
| 2011/0107524 A1 | 5/2011 | Chieffi et al. |
| 2011/0118691 A1 | 5/2011 | Nishitani |
| 2011/0139170 A1 | 6/2011 | Hippe et al. |
| 2011/0150815 A1 | 6/2011 | Woo et al. |
| 2011/0165107 A1 | 7/2011 | Derks et al. |
| 2011/0171155 A1 | 7/2011 | Federle |
| 2011/0177017 A1 | 7/2011 | Coffindaffer et al. |
| 2011/0232668 A1 | 9/2011 | Hoffmann et al. |
| 2011/0245126 A1 | 10/2011 | Tsaur et al. |
| 2011/0245134 A1 | 10/2011 | Smets |
| 2011/0245136 A1 | 10/2011 | Smets |
| 2011/0268778 A1 | 11/2011 | Dihora et al. |
| 2011/0269657 A1 | 11/2011 | Dihora |
| 2011/0300095 A1 | 12/2011 | Dente et al. |
| 2011/0303766 A1 | 12/2011 | Smith |
| 2011/0305739 A1 | 12/2011 | Royce |
| 2011/0305778 A1 | 12/2011 | Caggioni et al. |
| 2011/0308555 A1 | 12/2011 | Smets et al. |
| 2011/0308556 A1 | 12/2011 | Smets et al. |
| 2011/0319790 A1 | 12/2011 | Kost et al. |
| 2012/0004328 A1 | 1/2012 | Huchel et al. |
| 2012/0009285 A1 | 1/2012 | Wei et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0052031 A1 | 3/2012 | Troccaz et al. |
| 2012/0100091 A1 | 4/2012 | Hata et al. |
| 2012/0100092 A1 | 4/2012 | Murray |
| 2012/0129924 A1 | 5/2012 | Park et al. |
| 2012/0219610 A1 | 8/2012 | Smith, III et al. |
| 2012/0230936 A1 | 9/2012 | Mikkelsen |
| 2012/0237469 A1 | 9/2012 | Dente et al. |
| 2012/0246851 A1 | 10/2012 | Smith et al. |
| 2012/0258150 A1 | 10/2012 | Rauckhorst et al. |
| 2012/0291911 A1 | 11/2012 | Smith |
| 2012/0309660 A1 | 12/2012 | Kawasoe |
| 2012/0316095 A1 | 12/2012 | Wei et al. |
| 2013/0029932 A1 | 1/2013 | Kachi et al. |
| 2013/0034515 A1 | 2/2013 | Stone et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0266642 A1 | 10/2013 | Hollingshead et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall |
| 2013/0319463 A1 | 12/2013 | Policicchio |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda |
| 2014/0127149 A1 | 5/2014 | Lepilleur |
| 2014/0131395 A1 | 5/2014 | Chang |
| 2014/0134125 A1 | 5/2014 | Dahl et al. |
| 2014/0162979 A1 | 6/2014 | Palla-venkata et al. |
| 2014/0171471 A1 | 6/2014 | Krueger |
| 2014/0186864 A1 | 7/2014 | Kato et al. |
| 2014/0201927 A1 | 7/2014 | Bianchetti et al. |
| 2014/0216495 A1 | 8/2014 | Bureiko |
| 2014/0221269 A1 | 8/2014 | Sobel et al. |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2014/0349902 A1 | 11/2014 | Allef et al. |
| 2015/0017152 A1 | 1/2015 | Potechin et al. |
| 2015/0021496 A1 | 1/2015 | Shabbir |
| 2015/0037273 A1 | 2/2015 | Wagner |
| 2015/0050231 A1 | 2/2015 | Murase |
| 2015/0057208 A1 | 2/2015 | Frantz et al. |

(56) References Cited

U.S. PATENT DOCUMENTS

| | | |
|---|---|---|
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0108163 A1 | 4/2015 | Smith et al. |
| 2015/0110728 A1 | 4/2015 | Jayaswal |
| 2015/0141310 A1 | 5/2015 | Smets et al. |
| 2015/0147286 A1 | 5/2015 | Barrera |
| 2015/0157548 A1 | 6/2015 | De Feij et al. |
| 2015/0218496 A1 | 8/2015 | Schmiedel et al. |
| 2015/0231045 A1 | 8/2015 | Krohn et al. |
| 2015/0262354 A1 | 9/2015 | Periaswamy |
| 2015/0297489 A1 | 10/2015 | Kleinen et al. |
| 2015/0299400 A1 | 10/2015 | Wagner et al. |
| 2015/0313818 A1 | 11/2015 | Stagg |
| 2015/0352027 A1 | 12/2015 | Thomas et al. |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0089317 A1 | 3/2016 | Cetti et al. |
| 2016/0089318 A1 | 3/2016 | Cetti et al. |
| 2016/0089322 A1 | 3/2016 | Santos Nogueira et al. |
| 2016/0089462 A1 | 3/2016 | Frankenbach |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach et al. |
| 2016/0090556 A1 | 3/2016 | Frankenbach et al. |
| 2016/0090557 A1 | 3/2016 | Frankenbach et al. |
| 2016/0090558 A1 | 3/2016 | Frankenbach et al. |
| 2016/0092661 A1 | 3/2016 | Hollingshead et al. |
| 2016/0095804 A1 | 4/2016 | Xavier et al. |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0206522 A1 | 7/2016 | Ribaut et al. |
| 2016/0235643 A1 | 8/2016 | Mathonneau et al. |
| 2016/0250115 A1 | 9/2016 | Li et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0296656 A1 | 10/2016 | Scavone et al. |
| 2016/0303043 A1 | 10/2016 | Khoury |
| 2016/0306909 A1 | 10/2016 | Hollingshead et al. |
| 2016/0309871 A1 | 10/2016 | Torres Rivera et al. |
| 2016/0310369 A1 | 10/2016 | Thompson |
| 2016/0310370 A1 | 10/2016 | Smith |
| 2016/0310371 A1 | 10/2016 | Thompson |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Zhao |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao |
| 2016/0317424 A1 | 11/2016 | Kadir et al. |
| 2016/0326458 A1 | 11/2016 | Smets et al. |
| 2016/0338929 A1 | 11/2016 | Zasloff |
| 2016/0354300 A1 | 12/2016 | Thompson et al. |
| 2017/0066579 A1 | 3/2017 | Zillges |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0224607 A1 | 8/2017 | Li et al. |
| 2017/0239155 A1 | 8/2017 | Hartnett |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0273880 A1 | 9/2017 | Hertenstein |
| 2017/0278249 A1 | 9/2017 | Stofel |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2017/0333591 A9 | 11/2017 | Scavone et al. |
| 2017/0367963 A1 | 12/2017 | Kadir et al. |
| 2018/0004875 A1 | 1/2018 | Cetti et al. |
| 2018/0044097 A1 | 2/2018 | Zeik |
| 2018/0057451 A1 | 3/2018 | Owens et al. |
| 2018/0066210 A1 | 3/2018 | Frankenbach et al. |
| 2018/0098923 A1 | 4/2018 | Hutton, III |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | L'Oreal |
| 2018/0116941 A1 | 5/2018 | L'Oreal |
| 2018/0133133 A1 | 5/2018 | Kleinen et al. |
| 2018/0177708 A1 | 6/2018 | Lee et al. |
| 2018/0221266 A1 | 8/2018 | Zhao et al. |
| 2018/0256481 A1 | 9/2018 | Glenn, Jr |
| 2018/0280270 A1 | 10/2018 | Rughani et al. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2018/0360713 A1 | 12/2018 | Jouy et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0125650 A1 | 5/2019 | Lee et al. |
| 2019/0142711 A1 | 5/2019 | Torres Rivera |
| 2019/0142800 A1 | 5/2019 | Ghosh et al. |
| 2019/0155975 A9 | 5/2019 | Cetti et al. |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0328647 A1 | 10/2019 | Chang et al. |
| 2019/0365611 A1 | 12/2019 | Brown et al. |
| 2019/0365619 A1 | 12/2019 | Ceballos et al. |
| 2019/0365633 A1 | 12/2019 | Glenn, Jr. |
| 2020/0000690 A1 | 1/2020 | Renock |
| 2020/0078284 A1 | 3/2020 | Botto et al. |
| 2020/0129402 A1 | 4/2020 | Jamadagni |
| 2020/0163846 A1 | 5/2020 | Song |
| 2020/0170894 A1 | 6/2020 | Park et al. |
| 2020/0197272 A1 | 6/2020 | Hertenstein et al. |
| 2020/0206110 A1 | 7/2020 | Hertenstein et al. |
| 2020/0237628 A1 | 7/2020 | Torres Rivera |

(56) References Cited

U.S. PATENT DOCUMENTS

| | | | |
|---|---|---|---|
| 2021/0022986 A1 | 1/2021 | Glenn, Jr. | |
| 2021/0093543 A1 | 4/2021 | Parikh et al. | |
| 2021/0121385 A1 | 4/2021 | Muller et al. | |
| 2021/0128444 A1 | 5/2021 | Muller et al. | |
| 2021/0128447 A1* | 5/2021 | Galpin | A61K 8/368 |
| 2021/0169765 A1 | 6/2021 | Renock | |
| 2021/0212927 A1 | 7/2021 | Hutton, III et al. | |
| 2021/0267853 A1 | 9/2021 | Johnson et al. | |
| 2021/0275410 A1 | 9/2021 | Hutton, III | |
| 2021/0353518 A1 | 11/2021 | Ballhaus et al. | |
| 2021/0353522 A1 | 11/2021 | Ballhaus et al. | |
| 2021/0401716 A1 | 12/2021 | Gogineni et al. | |
| 2022/0062136 A1* | 3/2022 | Feng | A61K 8/44 |
| 2022/0160606 A1 | 5/2022 | Renock | |
| 2022/0175640 A1 | 6/2022 | Herteinstein et al. | |
| 2022/0323337 A1 | 10/2022 | Yamazaki | |
| 2022/0378680 A1 | 12/2022 | Ballhaus et al. | |
| 2022/0395444 A1 | 12/2022 | Hutton, III | |
| 2023/0053056 A1 | 2/2023 | Renock et al. | |

FOREIGN PATENT DOCUMENTS

| | | |
|---|---|---|
| CA | 704195 A | 2/1965 |
| CA | 1248458 A | 1/1989 |
| CA | 2078375 A1 | 3/1994 |
| CN | 1263455 A | 8/2000 |
| CN | 1286612 A | 3/2001 |
| CN | 1545404 A | 11/2004 |
| CN | 1823929 A | 8/2006 |
| CN | 100534415 C | 9/2009 |
| CN | 101112349 B | 5/2011 |
| CN | 101690697 B | 10/2011 |
| CN | 101559034 B | 1/2013 |
| CN | 102895151 A | 1/2013 |
| CN | 102973437 A | 3/2013 |
| CN | 102697668 B | 8/2013 |
| CN | 103356408 A | 10/2013 |
| CN | 102697670 B | 7/2014 |
| CN | 104107401 A | 10/2014 |
| CN | 102851015 B | 12/2014 |
| CN | 105726393 A | 7/2016 |
| CN | 105769617 A | 7/2016 |
| CN | 106659664 A | 5/2017 |
| CN | 106750361 A | 5/2017 |
| CN | 107595657 A | 1/2018 |
| CN | 107595673 A | 1/2018 |
| CN | 107648096 A | 2/2018 |
| CN | 107737329 A | 2/2018 |
| CN | 107961212 A | 4/2018 |
| CN | 108186385 A | 6/2018 |
| CN | 108283583 A | 7/2018 |
| CN | 108451858 A | 8/2018 |
| CN | 110279591 A | 9/2019 |
| CN | 113041184 A | 6/2021 |
| DE | 2145204 A1 | 3/1973 |
| DE | 3018456 A1 | 11/1981 |
| DE | 4315396 A1 | 11/1994 |
| DE | 102004012009 A1 | 9/2005 |
| DE | 202005009618 U1 | 9/2005 |
| DE | 102004023720 A1 | 12/2005 |
| DE | 102014225083 A1 | 10/2015 |
| DE | 102014225606 A1 | 10/2015 |
| DE | 102015204987 A1 | 9/2016 |
| EP | 0108517 A2 | 5/1984 |
| EP | 0574086 A2 | 12/1993 |
| EP | 0666358 A1 | 8/1995 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 1842572 A2 | 10/2007 |
| EP | 2005939 A1 | 12/2008 |
| EP | 1970045 A3 | 9/2009 |
| EP | 2042216 B1 | 9/2015 |
| EP | 3121210 A1 | 1/2017 |
| EP | 3260171 A1 | 12/2017 |
| EP | 3622946 A1 | 3/2020 |
| ES | 2052450 B1 | 12/1994 |
| FR | 2669531 A1 | 5/1992 |
| FR | 2795955 A1 | 1/2001 |
| GB | 190110699 A | 8/1901 |
| GB | 191023922 A | 10/1911 |
| GB | 1347950 A | 2/1974 |
| GB | 2048229 | 12/1980 |
| GB | 2450727 A | 1/2009 |
| HU | 42318 | 8/1986 |
| JP | S56011009 A | 12/1981 |
| JP | S58113300 A | 7/1983 |
| JP | S58198412 A | 11/1983 |
| JP | AS60004598 A | 1/1985 |
| JP | S61236708 A | 10/1986 |
| JP | S62205200 A | 9/1987 |
| JP | S63501221 A | 5/1988 |
| JP | S63165308 A | 7/1988 |
| JP | H04364114 A | 12/1992 |
| JP | H06220495 A | 8/1994 |
| JP | H0753340 A | 2/1995 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | H10017894 A | 1/1998 |
| JP | H11139944 A | 5/1999 |
| JP | 2964226 B2 | 10/1999 |
| JP | 2000178586 A | 6/2000 |
| JP | 3069802 B2 | 7/2000 |
| JP | 2001011492 A | 1/2001 |
| JP | 2001011497 A | 1/2001 |
| JP | 2001254099 A | 9/2001 |
| JP | 2001261529 A | 9/2001 |
| JP | 2003201217 A | 12/2001 |
| JP | 2002179552 A | 6/2002 |
| JP | 2002226889 A | 8/2002 |
| JP | 2002285191 A | 10/2002 |
| JP | 2002336337 A | 11/2002 |
| JP | 2003055699 A | 2/2003 |
| JP | 2003082398 A | 3/2003 |
| JP | 2003171688 A | 6/2003 |
| JP | 2003176497 A | 6/2003 |
| JP | 2003261413 A | 9/2003 |
| JP | 2003268398 A | 9/2003 |
| JP | 3480165 B2 | 12/2003 |
| JP | 2003342131 A | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006063044 A | 3/2006 |
| JP | 2006104149 A | 4/2006 |
| JP | 2006124312 A | 5/2006 |
| JP | 2006183039 A | 7/2006 |
| JP | 2006193549 A | 7/2006 |
| JP | 2006249092 A | 9/2006 |
| JP | 2006282565 A | 10/2006 |
| JP | 2007131687 A | 5/2007 |
| JP | 2007177047 A | 7/2007 |
| JP | 2007223935 A | 9/2007 |
| JP | 2007238607 A | 9/2007 |
| JP | 2007297380 A | 11/2007 |
| JP | 2008001626 A | 1/2008 |
| JP | 2008214292 A | 9/2008 |
| JP | 2009096778 A | 5/2009 |
| JP | 2009120559 A | 6/2009 |
| JP | 2009161866 A | 7/2009 |
| JP | 2010138130 A | 6/2010 |
| JP | 2011153167 A | 8/2011 |
| JP | 2011190221 A | 9/2011 |
| JP | 2011241353 A | 12/2011 |
| JP | 5041113 B2 | 7/2012 |
| JP | 2013010757 A | 1/2013 |
| JP | 2013091641 A | 5/2013 |

(56) References Cited

FOREIGN PATENT DOCUMENTS

| | | |
|---|---|---|
| JP | 2013151434 A | 8/2013 |
| JP | 2013155143 A | 8/2013 |
| JP | 2013193968 A | 9/2013 |
| JP | 2013216639 A | 10/2013 |
| JP | 6046394 B2 | 1/2014 |
| JP | 2014009177 A | 1/2014 |
| JP | 2014024875 A | 2/2014 |
| JP | 2014037383 A | 2/2014 |
| JP | 2014091723 A | 5/2014 |
| JP | 2014234350 A | 12/2014 |
| JP | 5667790 B2 | 2/2015 |
| JP | 2015034157 A | 2/2015 |
| JP | 2015101545 A | 6/2015 |
| JP | 2015129099 A | 7/2015 |
| JP | 2016013973 A | 1/2016 |
| JP | 2016030722 A | 3/2016 |
| JP | 2016088910 A | 5/2016 |
| JP | 6184550 B1 | 8/2017 |
| JP | 2018012673 A | 1/2018 |
| JP | 2018083781 A | 5/2018 |
| KR | 100290589 B1 | 9/2001 |
| KR | 100821846 B1 | 4/2008 |
| KR | 1020080111280 A | 12/2008 |
| KR | 20090095359 A | 9/2009 |
| KR | 20100040180 A | 4/2010 |
| KR | 20140060882 A | 5/2014 |
| KR | 101494008 B1 | 2/2015 |
| KR | 101503922 B1 | 3/2015 |
| KR | 101532070 B1 | 7/2015 |
| UA | 50333 U | 5/2010 |
| WO | 8603679 A1 | 7/1986 |
| WO | 9114759 A1 | 10/1991 |
| WO | 91017237 A1 | 11/1991 |
| WO | 9213520 A1 | 8/1992 |
| WO | 199325650 A1 | 12/1993 |
| WO | 9417783 A2 | 8/1994 |
| WO | 9502389 A2 | 1/1995 |
| WO | 9726854 A1 | 7/1997 |
| WO | 9823258 A1 | 6/1998 |
| WO | 9906010 A2 | 2/1999 |
| WO | 9918928 A1 | 4/1999 |
| WO | 9924004 A1 | 5/1999 |
| WO | 9924013 A1 | 5/1999 |
| WO | 9949837 A1 | 10/1999 |
| WO | 9957233 A1 | 11/1999 |
| WO | 0012553 A1 | 3/2000 |
| WO | 0032601 | 6/2000 |
| WO | 0119949 A1 | 3/2001 |
| WO | 0142409 A1 | 6/2001 |
| WO | 0148021 A1 | 7/2001 |
| WO | 2001076552 A2 | 10/2001 |
| WO | 2003051319 A1 | 6/2003 |
| WO | 03096998 A1 | 11/2003 |
| WO | 03105793 A2 | 12/2003 |
| WO | 2004078901 A1 | 9/2004 |
| WO | 2005023975 A1 | 3/2005 |
| WO | 2008017540 A1 | 2/2008 |
| WO | 2008128826 A1 | 10/2008 |
| WO | 2008145582 A1 | 12/2008 |
| WO | 2009016555 A2 | 2/2009 |
| WO | 2009030594 A1 | 3/2009 |
| WO | 2009053931 A2 | 4/2009 |
| WO | 2010026009 A1 | 3/2010 |
| WO | 2010052147 A2 | 5/2010 |
| WO | 2011124560 A2 | 10/2011 |
| WO | 2012017091 A2 | 2/2012 |
| WO | 2012052536 A2 | 4/2012 |
| WO | 2012055587 A1 | 5/2012 |
| WO | 2012055812 A1 | 5/2012 |
| WO | 2012084970 A1 | 6/2012 |
| WO | 2012127009 A1 | 9/2012 |
| WO | 2012136651 A1 | 10/2012 |
| WO | 2013010706 A2 | 1/2013 |
| WO | 2013018805 A1 | 2/2013 |
| WO | 2013119908 A1 | 8/2013 |
| WO | 2014073245 A1 | 5/2014 |
| WO | 2014073456 A1 | 5/2014 |
| WO | 2014111667 A2 | 7/2014 |
| WO | 2014111668 A2 | 7/2014 |
| WO | 2014148245 A1 | 9/2014 |
| WO | 2015016037 A1 | 2/2015 |
| WO | 2015067779 A1 | 5/2015 |
| WO | 2015085376 A1 | 6/2015 |
| WO | 2015122371 A1 | 8/2015 |
| WO | 2015141787 A1 | 9/2015 |
| WO | 2016049389 A1 | 3/2016 |
| WO | 2016147196 A1 | 9/2016 |
| WO | 2017052161 A1 | 3/2017 |
| WO | 2017140798 A1 | 8/2017 |
| WO | 2017140802 A1 | 8/2017 |
| WO | 2017207685 A1 | 12/2017 |
| WO | 2018023180 A1 | 2/2018 |
| WO | 2018064511 A1 | 4/2018 |
| WO | 2018109148 A1 | 6/2018 |
| WO | 2019030458 A2 | 2/2019 |
| WO | 2019074990 A1 | 4/2019 |
| WO | 2019074992 A1 | 4/2019 |
| WO | 2019200027 A1 | 10/2019 |
| WO | 2020005309 A1 | 1/2020 |
| WO | 2020030732 A1 | 2/2020 |
| WO | 2020076881 A1 | 4/2020 |
| WO | 2020131836 A1 | 6/2020 |
| WO | 2021026572 A1 | 2/2021 |
| WO | 2021099088 A1 | 5/2021 |
| WO | 2021127318 A1 | 6/2021 |
| WO | 2021144326 A1 | 7/2021 |
| WO | 2021231510 A1 | 11/2021 |
| WO | 2022144161 A1 | 7/2022 |
| WO | 2024037872 A1 | 2/2024 |

OTHER PUBLICATIONS

"Natural Detangling Shampoo", Mintel Database, dated Sep. 13, 2017; 2 pages.
"Soda Shampoo", Mintel Database, dated Apr. 2015; pp. 1-4.
"Treatment Foam for Recurrent Scaling Conditions", Mintel Database, Aug. 2007; pp. 1-2.
Acne Foaming Cleanser, Database accession No. 4172863, Jul. 29, 2016, 3 pages.
Air Quality of the Iowa Department of Natural Resources. A Review of the Science and Technology of Odor Measurement, 2005, 51 pages (2005).
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018; 1 page.
Anonymous: "Naturally Derived Body Wash", Database GNPD [Online] MINTEL; Feb. 15, 2021, 2 pages.
Anonymous: "Peptide Shampoo", Database GNPD [Online] MINTEL; Dec. 14, 2015, 3 pages.
Anonymous: "Replenishing Moisture Shampoo", Database GNPD [Online] MINTEL, Mar. 2, 10015br.
Anonymous: "Shampoo", Database GNPD [Online] MINTEL, Jan. 26, 2021, 3 pages.
Anonymous: "Shampooing au Phytolait d'abricot—Formule N°102-MP06-MI3-AA03",Internet Citation, Feb. 19, 2005, Retrieved from the Internet: URL: http://web.archive.org/web/20050219040350/www.albanmuller.com/francais/catalogue/formules/formul10.asp, 1 page.
ASTM D3954-94, Reapproved 2010, vol. 15.04, Standard Test Method for Dropping Point of Waxes.
BASF, "Practical Guide to Rheology Modifiers", download from https://insights.basf.com/files/BASF_ED_RheologyModifiers_download.pdf on Nov. 1, 2022. (Year: 2022).
Brattoli et al. Odour Detection Methods: Offactometry and Chemical Sensors. Sensors (Basel), 2011; 11(5); 5290-5322 (2011).
Carbopol Aqua SF-1 Polymer Technical Data Sheet, TDS-294, dated Dec. 2000 ; pp. 1-9.
Chemical Book (Chemical Book, Isolongifolone, available at http://www.chemicalbook.com/ProductChemicalPropertiesCB5318980_EN.htm), no date available.

(56) References Cited

OTHER PUBLICATIONS

Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
Crepaldi, E.L., et al., Chemical, Structural, and Thermal Properties of Zn(II)—Cr(III) Layered Double Hydroxides Intercalated with Sulfated and Sulfonated Surfactants, Journal of Colloid and Interface Science, 2002, pp. 429-442, vol. 248.
D'Souza et al., Shampoo and Conditioners: What a Dermatologist Should Know? Indian J Dermatol, dated May-Jun. 2015; pp. 60(3), 248-254 (2015).
Database GNPD [Online] MINTEL;Mar. 28, 2018 (Mar. 28, 2018), anonymous: Dandruff Control Shampoo 11,XP055787038, Database accession No. 5556267 abstract.
Database GNPD [Online] MINTEL; Apr. 5, 2005 (Apr. 5, 2005), anonymous: "Anticaspa-Graso Anti-DandruffShampoo",XPC:155787029, Database accession No. 351776paragraph [ingredients].
Database GNPD [Online] MINTEL; Jan. 6, 2020 (Jan. 6, 2020), anonymous: 11 Shampoo 11, 3 pages.
Database WPI; Week 201459; Thomson scientific, London, GB; An 2014-P66521; XP002752638.
Datasheet: Empigen Total Active TC/U, Datasheet, dated Jan. 31, 2017 (Innospec) ; 2 pages.
Dehyquart Guar: Published dated Nov. 2010 ; pp. 1-34.
Fevola, Michael J. "Guar Hydroxypropyltrimonium Chloride." Cosmetics and toiletries; vol. 127.1; Jan. 2012 ; pp. 16-21.
Grillet et al., "Polymer Gel Rheology and Adhesion", Rheology, 2012, pp. 59-80.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet: URL:https://www.happi.com/contents/view_formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
McGinley et al. American Association of Textile Chemists and Colorists, 2017, 17 pages, (2017).
McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Morioka, H. et al. "Effects of Zinc on the New Preparation Method of Hydroxy Double Salts" Inorg. Chem. 1999, 38, 4211-6.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
Parchem fine & specialty chemicals. MIPA-laureth sulfate supplier distributor—CAS 83016-76-6; dated 2021; pp. 1-7.
PERM Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-theSafety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Sheet for Chemoryl™LS Surfactant, Sodium Lauroyl Sarcosinate, Lubrizol Advanced Materials, Inc., Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007 (Jan. 1, 2007), XP055799133, pp. 1476-1478.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Sensory., "A Review of The Science and Technology of Odor Measurement", Prepared for the Air Quality Bureau of the Iowa Department of Natural Resources, Dec. 30, 2005 51 pages.
Shampoo C, Database accession No. 1632217, Sep. 29, 2011, 3 pages.
Softazoline CL-R, Kawaken Singapore PTE Ltd. Website printout from http://kawaken.com.sg/softazoline-ch-r//a, accessed on Nov. 30, 2022.
Todd et al., Volatile Silicone Fluids for Cosmetics, Cosmetics and Toiletries, vol. 91, pp. 27-32 (Jan. 1976).
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates andGuidelines of Corona Virus View project health and beauty science View project Rohit Bhavsar Reliance Industries Limited; International Journal for Research inApplied Science & Engineering Technology, Apr. 1, 2020 (Apr. 1, 2020)t XP055842327, DOI: 10.22214, 14 pages.
"Deep Image Matting", Ning Xu et al, Beckman Institute for Advanced Science and Technology, University of Illinois at Urbana-Champaign, Adobe Research, dated Mar. 10, 2017; 10 pages.
Anonymous: "Anti-Dandruff Scalp Care Shampoo", MINTEL, Database accession No. 301924, Sep. 16, 2004, 2 pages.
"Personal care solutions Guide", Solvay, Publication date: May 2018, 84 pages.
Product Data Record Tego®Betain F KB 5, dated Jul. 1, 2015, 4 pages.

(56) References Cited

OTHER PUBLICATIONS

16158 PCT Search Report and Written Opinion for PCT/US2022/028256 dated Oct. 7, 2022,15 pages.
PubChem CID 3033856 for decyl glucoside. downloaded Jun. 22, 2023, 32 pages. (Year: 2023).
"Comparative Study on the Chemical constituents of Aloe Vera and Aloe Kula in China", Zhang Xiaohua et al., Flavor Cosmetics, No. 63, dated Dec. 31, 2000, pp. 7-11.
Shampoo, ID# 6148479. Mintel GNPD [online], URL: http://www.gnpd.com, Nov. 2018, 4 pages.
Anonymous, "Medicated Cleanser", Nioxin Research Laboratories, Mintel GNPD [online], ID:1060983, URL: http://www.gnpd.com, dated Feb. 2009, 4 pages.
P. A. Cornwell, "A review of shampoo surfactant technology: consumer benefits, raw materials and recent developments", International Journal of Cosmetic Science, 40, Oct. 27, 2017, pp. 16-30.
Sbhatu et al, "Formulation and Physicochemical Evaluation of Lab-Based Aloe adigratana Reynolds Shampoos", Hindawi, International Journal of Analytical Chemistry, vol. 2020, Article ID 6290617, URL: https://www.ncbi.nlm.nih.gov/pmc/articles/PMC7160718/, Published Apr. 4, 2020, 7 pages.
Shampoo Manufacturing Plant, Lodha International, URL: https://www.lodhapharma.com/shampoo-manufacturing-plant.php#:~:text=Shampoos%20are%20categorized%20as%20viscous,if%20not%20all%20of%20them, Published: 2018, 4 pages.
"Jaguar® Optima", Solvay, site: www.solvay.com, year 2023, 1 page.
Cafasso, "What's the proper order to use shampoo and conditioner while bathing", Healthline, Retrieved from Internet: https://www.healthline.com/health/beauty-skin-care/shampoo-or-conditioner-first, dated Jul. 13, 2020, 2 pages.
Duis et al., "Environmental fate and effects of water-soluble synthetic organic polymers used in cosmetic products", Enviromental Sciences Europe, 33:21, Year 2021; 20 pages.
Matsouka et al., "Vesicle formation of disodium lauryl sulfosuccinate", Journal of Molecular Liquids, 348, 118422, Nov. 1, 2021, 7 pages.
Ramachandra et al., "Processing of Aloe Vera Leaf Gel: A Review", American Journal of Agricultural and Biological Sciences 3 (2), year 2008, pp. 502-510.
Yang et al., "Synthesis and foaming performance of Lauramidopropyl Betaine Derivate Surfactants", Materials Science Forum, vol. 953, Jan. 9, 2019, 1 page.
Anonymous, "Healing + Anti-Breakage Shampoo", ID# 3383875, Mintel Gnpd, URL: http://www.gnpd.com, dated Aug. 2015, 3 pages.
Anonymous, "Shampoo", ID# 1743027, Mintel GNPD, URL: http://www.gnpd.com, dated Mar. 2012, 3 pages.
Anonymous; "Advanced Oil Control Anti Dandruff Shampoo", XP093149356, Database GNPD Mintel, Database accession No. 9347772, dated Feb. 1, 2022, 03 Pages.
Bryant Taylor, "Here's What You Need To Know About The Latest Korean Beauty Obsession", Retrieved from Internet: https://www.refinery29.com/en-us/scalp-ph-facts, Jun. 5, 2016, 8 pages.
Goh et al., "New cationic conditioning polymers for hair care", Retrieved from Internet: https://cosmeticsbusiness.com/new-cationic-conditioning-polymers-for-hair-care-47152, Dec. 18, 2006, 10 pages.
Harvey Gedeon; Journal of Cosmetic Science, "The Challenges Facing Today's Cosmetic Chemist", 57, 2005, 73-94 (22 pages).
Hossel et al. "Conditioning polymers in today's shampoo formulations-efficacy, mechanism and test methods", International Journal of Cosmetic Science. 2000, vol. 1, 2000, pp. 1-10.
Manuel, F. et al., "A new postulate on two stages of dandruff: A clinical perspective", International Journal of Trichology, 2011, vol. 3, 3-6 (Year: 2011).
Tarun et al. "Evaluation of pH of Bathing Soaps and Shampoos for Skin and Hair Care", Indian Journal of Dermatology. 2014, vol. 59, No. 5, No Known Date, 6 Pages.
Technical Information; TEGO® Betain F KB 5 / TEGO® Betain F KM 1; Mild amphoteric surfactants: www.evonik.com/personal-care; Jul. 2010; 2 pages; Product Specification; 5 pages.
"Selecting the Right Surfactant for Cosmetics", Retrieved from Internet: https://cosmetics.specialchem.com/centers/selecting-the-right-surfactantforcosmetics/surfactantsinhaircareapplications#:~:text=Amphoteric%20surfactants%20are %20used%20to,be%20based%20ntirely%20on%20amphoterics, Aug. 11, 2020, 4 pages.
"UltraPureGel", Retrieved from Internet: https://www.ingredientstodiefor.com/item/UltraPureGel/1264,pages.

* cited by examiner

SHAMPOO COMPOSITIONS CONTAINING A SULFATE-FREE SURFACTANT SYSTEM AND SCLEROTIUM GUM THICKENER

FIELD OF THE INVENTION

The present invention relates to a shampoo composition, in particular a phase-stable shampoo composition with a surfactant system that is free of or substantially free of sulfate-based surfactants and a thickener comprising sclerotium gum.

BACKGROUND OF THE INVENTION

Historically, most commercial cleansing compositions, such as shampoo compositions, contain sulfate-based surfactant systems because they provide effective cleaning and a good user experience. Sulfate-based surfactant systems generally have acceptable viscosity making it easy to apply and distribute the shampoo composition throughout a user's hair. In addition, sulfate-based surfactant systems can generally be paired with cationic polymers that can form coacervate with the sulfate-based surfactant system during use thereby providing a shampoo with effective conditioning benefits.

Some consumers, especially those with color-treated or otherwise treated hair, may prefer a shampoo composition that is substantially free of sulfate-based surfactant systems. However, it can be difficult to formulate a shampoo with non-sulfate-based surfactants with sufficient viscosity. Many current sulfate-free shampoos have a viscosity that is too low, which makes it difficult to hold in a user's hand and apply across the hair and scalp. These consumers may also want conditioning polymers in their shampoo because higher conditioning shampoos feel less stripping to the hair. However, it can be difficult to formulate a shampoo with a sulfate-free surfactant system that also has cationic polymers that deliver a conditioning benefit because the shampoo can have low viscosity, which makes it difficult for a user to hold the liquid shampoo composition in their palm and distribute across their hair and scalp.

When traditional anionic thickeners, such as xanthan gum, carrageenan, konjac gum, and gellan gum are added to shampoo compositions containing sulfate-free surfactants and cationic polymers, the composition can be unstable and separate into multiple phases. The traditional anionic thickener can complex with the cationic polymer, thereby reducing active deposition, which decreases wet conditioning and causes phase separation.

Therefore, there is a need for a stable shampoo composition with a sufficient viscosity and superior product performance that contains one or more non-sulfated anionic surfactants.

SUMMARY OF THE INVENTION

A stable shampoo composition comprising: (a) a surfactant system comprising: (i) from about 3 to about 35% of an anionic surfactant; (ii) from about 5 to about 15% of an amphoteric surfactant; wherein the surfactant system is substantially free of sulphated surfactants; (b) from about 0.01% to about 2% of a cationic polymer; (c) from about 0.15% to about 1.5% of a thickener comprising sclerotium gum; wherein the composition comprises a viscosity greater than 2500 cP and a pH greater than 5.5.

DETAILED DESCRIPTION OF THE INVENTION

Figure 1:
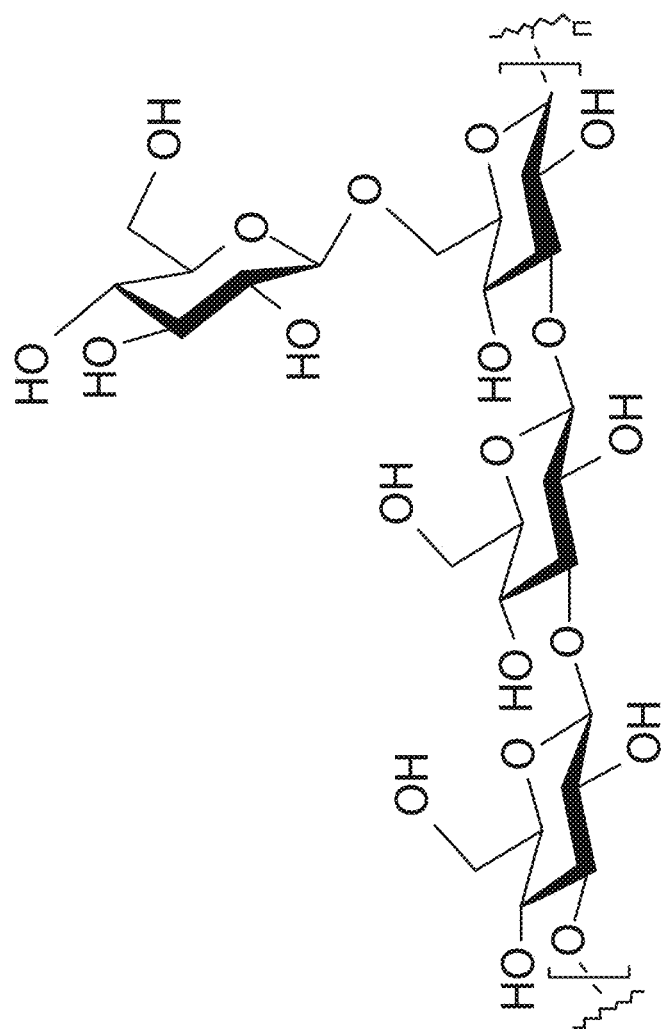
FIG. 1 shows a typical sclerotium gum structure.

Some consumers prefer shampoo compositions that are substantially free of sulfate-based surfactants. These consumers may also prefer shampoos that feel less stripping to the hair and therefore may prefer a shampoo with cationic conditioning polymers. However, it is difficult to formulate these compositions to be stable and have a consumer preferred viscosity. They are often too thin, which makes them difficult to hold in a user's palm and distribute across their hair and scalp.

There are at least three common ways to thicken shampoo compositions:
1. Add an anionic thickener (e.g. xanthan gum, carrageenan, konjac gum, gellan gum)
2. Decrease the pH
3. Add inorganic salts (e.g. NaCl)

However, these methods are not effective in a shampoo composition that contains sulfate-free anionic surfactants and a cationic conditioning polymer. First, when traditional anionic thickeners are added, it was found that the composition becomes unstable, impacting product appearance and performance Second, when the pH was decreased it was found that many sulfate-free surfactant systems can hydrolyze at low pH resulting in viscosity and performance changes over time and will eventually lead to phase separation. Third, when inorganic salt was added to the liquid shampoo becomes unstable due to formation of a gel-like complex known as coacervate in the composition (referred to herein as "in situ coacervate" or an "in situ coacervate phase," which is a coacervate that forms in the composition, prior to dilution), as opposed to when it is diluted with water when a user washes their hair.

It was found that sclerotium gum, which has a unique triple helix structure, could be used to thicken shampoo compositions that contain sulfate-free anionic surfactants and cationic polymers while also maintaining phase stability. It was also found that a thickener comprising sclerotium gum could be used to thicken shampoo compositions that contain sulfate-free surfactants and cationic polymers while also maintaining phase stability and pH (e.g. >5.5), and providing superior wet conditioning.

It was also found that in some examples the amount of inorganic salt in the composition can also impact product stability and viscosity. In some examples, product stability and acceptable viscosity can be achieved by (1) maintaining a low inorganic salt concentration in formulas (e.g. from about 0 to about 1 wt %); and/or (2) having a ratio of polymer charge density to salt of greater than 1.2:1.

One way to lower the inorganic salt concentration is to avoid or minimize adding extra inorganic salt to the formula and/or by using low inorganic salt containing raw materials. For example, commercially available sulfate free surfactants such as disodium cocoyl glutamate typically comes with high levels of inorganic salt such as 5% or higher Amphoteric surfactant such as betaines or sultaines also typically come with high levels of inorganic salt such as sodium chloride. Use of these high salt containing raw materials in sulfate-free surfactant based cleaning formulations in excess of about 1% total sodium chloride in the formulation can cause formation of undesired coacervate in the product. If the inorganic salt level is lowered in the surfactant raw materials so that total salt in the composition is less than about 1% or lower, a stable 1-phase clear product can be formulated. Whereas, if the regular material with high inorganic salt is used, the product is cloudy, 2-phase, and unstable. The cloudy 2-phase product is likely the result of in situ coacervate formation.

In some examples, sclerotium gum can be the only thickener in the shampoo composition. In other examples, the thickener can include sclerotium gum, inorganic salt, and combinations thereof. The shampoo composition can be free of or substantially free of anionic thickeners. Non-limiting examples of anionic thickeners that may be excluded from the shampoo compositions can include carboxylic acid polymers, crosslinked polyacrylate polymers, polyacrylamide polymers, polysaccharides, and gums. Non-limiting examples of gums can include acacia, agar, algin, alginic acid, ammonium alginate, amylopectin, calcium alginate, calcium carrageenan, carrageenan, dextrin, gelatin, gellan gum, karaya gum, konjac gum, locust bean gum, natto gum, potassium alginate, potassium carrageenan, propylene glycol alginate, sodium carboxymethyl dextran, sodium carrageenan, tragacanth gum, xanthan gum, and mixtures thereof.

The pH can be greater than 5.5, alternatively greater than 5.7, alternatively greater than 5.8. Alternatively, the pH can be from about 5 to about 8, alternatively from about 5.2 to about 7.5, alternatively from about 5.3 to about 7.25, alternatively from about 5.4 to about 7.1, alternatively from about 5.5 to about 7, alternatively from about 5.6 to about 6.9, alternatively from about 5.7 to about 6.8, and alternatively from about 5.8 to about 6.7. The pH can be from about 4 to about 8, alternatively from about 4.5 to about 7.5, alternatively from about 5 to about 7, alternatively from about 5.5 to about 6.5, alternatively from about 5.5 to about 6, and alternatively from about 6 to about 6.5. The pH is determined by the pH Test Method, described herein.

The shampoo composition can have a viscosity greater than 2500 cP, alternatively greater than 4000 cP, alternatively greater than 4500 cP, and alternatively greater than 5000 cP. The shampoo composition can have a viscosity of about 2500 cP to about 20,000 cP, alternatively from about 3000 cps to about 15,000 cps, alternatively from 4000 cP to about 13,000 cP, alternatively from about 5,000 cP to about 11,000 cP, and alternatively from about 7,000 cP to about 10,000 cP, alternatively from about 2500 cP to about 8500 cP, alternatively 2500 cP to about 6500 cP as measured at 26.6° C., as measured by the Cone/Plate Viscosity Measurement Test Method, described herein.

The shampoo composition can have a yield stress, Herschel-Bulkley @ shear rate $10^{-2}$ to $10^{-4}$ s$^{-1}$ of from about 0.001 Pa to about 0.5 Pa, alternatively from about 0.002 Pa to about 0.3 Pa, alternatively from about 0.003 Pa to about 0.2 Pa, alternatively from about 0.004 Pa to about 0.18 Pa, alternatively from about 0.007 Pa to about 0.17 Pa, and alternatively from about 0.008 Pa to about 0.15 Pa. The shampoo composition can have a yield stress, Herschel-Bulkley @ shear rate $10^{-2}$ to $10^{-4}$ s$^{-1}$ of greater than 0.003 Pa, alternatively greater than 0.005 Pa, alternatively greater than 0.010 Pa, alternatively greater than 0.015 Pa, and alternatively greater than 0.1 Pa. The yield stress is measured at 26.7° C. by flow sweep at a shear rate 100 to $10^{-4}$ s$^{-1}$ using Discovery Hybrid Rheometer (DHR-3) available from TA Instruments. To apply the Hershel-Bulkley model, the TA software to fit the model in the log space at a shear rate from $10^{-2}$ to $10^{-4}$ s$^{-1}$ is used. The geometry used to measure the yield stress and viscosity of the cleansing phase is a 60 mm 2° aluminum cone (with a Peltier steel plate). The geometry should be run at the gap specified by the manufacturer for the geometry. Trimming the sample during the initial conditioning step in step 1 is recommended to ensure data integrity and reproducibility. Torque map the geometry prior to running the yield stress or shear stress methods when the instrument+geometry is out of calibration. The version of Trios software used to generate the rheology data herein is TRIOS 5.1.1 In some examples, it was found that a thickener that contained a combination of sclerotium gum and citrus peel fiber (commercially available as FiberDesign™ Sensation from Cargill® with an INCI citrus limon peel powder (and) sclerotium gum) the shampoo composition could have a higher yield stress, which can help suspend actives (e.g. cationic polymers; silicones; non-silicone organic conditioning agents such as botanical hydrocarbon oils, waxes, conditioning polymers; anti-dandruff actives) in the formulation, which can lead to improved product performance. In some examples the thickener can be selected from the group consisting of sclerotium gum, citrus limon peel powder, inorganic salts, and combinations thereof. In other examples the thickener can be selected from the group consisting of sclerotium gum, citrus limon peel powder, and combinations thereof. In other examples, the thickener can contain both sclerotium gum and citrus limon peel powder.

The shampoo composition may have less than 1% of inorganic salt, alternatively less than 0.75% inorganic salt, alternatively less than 0.5% inorganic salt, alternatively less than 0.25% inorganic salt, alternatively less than or equal to 0.2% inorganic salt. The shampoo composition may have from about 0% to about 1% inorganic salt, alternatively from about 0% to about 0.9% inorganic salt, alternatively from about 0% to about 0.8%, alternatively from about 0% to about 0.5% inorganic salt, alternatively from about 0% to about 0.3% inorganic salt; and alternatively from about 0.05% to about 0.2% inorganic salt. The shampoo composition may have greater than 0% and less than 1% inorganic salt, alternatively greater than 0% and less than 0.75%, alternatively greater than 0% and less than 0.5%, and alternatively greater than 0% and less than 0.25%. The shampoo composition can include from about 0.5% to about 5% inorganic salt, alternatively from about 0.55% to about 4%, alternatively about 0.75% to about 3.5%, alternatively 0.6% to about 3.25%, alternatively from about 0.8% to about 3%, alternatively from about 0.8% to about 2.5%, alternatively from about 1% to about 2%, and alternatively from about 1% to about 1.5%. The shampoo composition can include from about 0.75% to about 1.5% inorganic salt, alternatively from about 0.8% to about 1.4%, alternatively from about 0.9% to about 1.4%. The wt. % inorganic chloride salt can be determined by the Argentometry Method to Measure wt % Inorganic Chloride Salt Test Method, described herein. The inorganic salt can be an inorganic chloride salt. The inorganic salt can enter the composition with the surfactants or other ingredients, or it can be added separately as a thickener. If the inorganic salt enters the composition along with the surfactants, it can still considered a thickener.

The ratio of polymer charge density to total inorganic salt can be from about 0.5:1 to about 3:1, from about 0.7:1 to about 2.5:1, alternatively 0.75:1 to about 2.25:1, alternatively from about 1:1 to about 2:1, alternatively from about 1.2:1 to about 1.5:1, alternatively from about 1.1:1 to about 1.4:1, and alternatively from about 1.2:1 to about 1.4:1. The ratio of polymer charge density to total inorganic salt can be ≥1.1:1, alternatively ≥1.2:1, alternatively ≥1.3:1, and alternatively ≥1.5:1. The ratio of polymer charge density to total inorganic salt can be <15:1, <10:1, <7:1, <5:1, alternatively <4:1, alternatively <3:1, alternatively <2:1, and alternatively <1.5:1. The ratio of polymer charge density to inorganic salt is the charge density of the cationic polymer (meq/gm) to the wt. % of the inorganic salt, disregarding the units. If the composition contains more than one cationic polymer, then the ratio is calculated according to the polymer with the lowest charge density.

The ratio of anionic surfactant to amphoteric surfactant can be from about 0.25:1 to about 3:1, alternatively from about 0.3:1 to about 2.5:1, alternatively from about 0.4:1 to about 2:1, alternatively from about 0.5:1 to about 1.5:1, alternatively from about 0.6:1 to about 1.25:1, and alternatively from about 0.75:1 to about 1:1. The ratio of anionic surfactant to amphoteric surfactant can be from about 0.4:1 to about 1.25:1, alternatively from about 0.5:1 to about 1.1:1, and alternatively from about 0.6:1 to about 1:1. In some examples, the ratio of anionic surfactant to amphoteric surfactant is less than 2:1, alternatively less than 1.75:1, alternatively less than 1.5:1, alternatively less than 1.1:1, and alternatively less than 1:1.

The shampoo composition can be used to clean and/or condition hair. First, the user dispenses the liquid shampoo composition from the bottle into their hand or onto a cleaning implement. Then, they massage the shampoo into their wet hair. While they are massaging the shampoo composition into the hair the shampoo is diluted and a coacervate can form and the shampoo can lather. After massaging into hair, the shampoo composition is rinsed from the user's hair and at least a portion of the cationic polymers can be deposited on the user's hair, which can provide a wet conditioning benefit. Shampooing can be repeated, if desired, and/or a conditioner can be applied. The conditioner can be a rinse-off conditioner or a leave-in conditioner.

It may be consumer desirable to have a shampoo composition with a minimal level of ingredients. The shampoo composition can be formulated without polymeric thickeners or suspending agents such as carbomer, EGDS or thixcin. The shampoo composition may contain 11 or fewer ingredients, 10 or fewer ingredients, 9 or fewer ingredients, 8 or fewer ingredients, 7 or fewer ingredients, 6 or fewer ingredients. The minimal ingredient formula can include water, anionic surfactant, amphoteric surfactant, cationic polymer, inorganic salt, and perfume. It is understood that perfumes can be formed from one or more materials. In some examples, the composition can be free of or substantially free of fragrance. In another example, the composition can be free of or substantially free of polyethylene glycol (PEG).

The composition can be free of alkyl polyglucoside. Non-limiting examples of alkyl polyglucosides can include decyl glucoside, cocoyl glucoside, lauroyl glucoside and combinations thereof. It has been found that alky polyglucosides can impact lather properties and thickening of shampoo compositions containing sulfate-free anionic surfactants and cationic conditioning polymers.

The composition can be substantially free of or free of fatty esters having at least 10 carbon atoms. The composition can be substantially free of or free of fatty esters. The composition can be substantially free of or free of fatty esters with hydrocarbyl chains derived from fatty acids or alcohols. The composition can be substantially free of or free of oligomeric or polymeric esters, prepared from unsaturated glyceryl esters can also be used as conditioning materials.

While the specification concludes with claims particularly pointing out and distinctly claiming the invention, it is believed that the present disclosure will be better understood from the description.

As used herein, "cleansing composition" includes personal cleansing products such as shampoos, conditioners, conditioning shampoos, shower gels, liquid hand cleansers, facial cleansers, and other surfactant-based liquid compositions.

The shampoo composition can be clear prior to dilution with water. The term "clear" or "transparent" as used herein, means that the compositions have a percent transparency (% T) of at least about 70% transmittance at 600 nm. The % T may be at 600 nm from about 70% to about 100%, from about 75% to about 100%, from about 80% to about 100%, from about 85% to about 100%, from about 90% to about 100%, from about 95% to about 100%. In the present invention, the percent transparency (% T) may be at least about 80% transmittance at 600 nm; percent transparency (% T) may be at least about 90% transmittance at 600 nm.

As used herein, the term "fluid" includes liquids and gels.

As used herein, "molecular weight" or "M.Wt." refers to the weight average molecular weight unless otherwise stated. Molecular weight is measured using industry standard method, gel permeation chromatography ("GPC"). The molecular weight has units of grams/mol.

As used herein, "substantially free" refers to less than 0.5%, alternatively less than 0.25%, alternatively less than 0.1%, alternatively less than 0.05%, alternatively less than 0.02%, and alternatively less than 0.01%.

As used herein, "sulfate free" and "substantially free of sulfates" means essentially free of sulfate-containing compounds except as otherwise incidentally incorporated as minor components.

Sulfate free contains no detectable sulfated surfactants.

As used herein, "sulfated surfactants" or "sulfate-based surfactants" means surfactants which contain a sulfate group. The term "substantially free of sulfated surfactants" or "substantially free of sulfate-based surfactants" means essentially free of surfactants containing a sulfate group except as otherwise incidentally incorporated as minor components.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Surfactant

The cleansing compositions described herein can include one or more surfactants in the surfactant system. The one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a cleansing composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

Cleansing compositions typically employ sulfate-based surfactant systems (such as, but not limited to, sodium lauryl sulfate) because of their effectiveness in lather production, stability, clarity and cleansing. The cleansing compositions described herein are substantially free of sulfate-based surfactants. "Substantially free" of sulfate based surfactants as used herein means from about 0% to about 3%, alternatively from about 0% to about 2%, alternatively from about 0% to about 1%, alternatively from about 0% to about 0.5%, alternatively from about 0% to about 0.25%, alternatively from about 0% to about 0.1%, alternatively from about 0% to about 0.05%, alternatively from about 0% to about 0.01%, alternatively from about 0% to about 0.001%, and/or alternatively free of sulfates. As used herein, "free of" means 0%.

Additionally, the surfactants can be added to the composition as a solution, instead of the neat material and the solution can include inorganic salts that can be added to the formula. The surfactant formula can have inorganic salt that can be from about 0% to about 2% of inorganic salts of the final composition, alternatively from about 0.1% to about 1.5%, and alternatively from about 0.2% to about 1%.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

The concentration of the surfactant in the composition should be sufficient to provide the desired cleaning and lather performance. The cleansing composition can include a total surfactant level of from about 5% to about 50%, alternatively from about 8% to about 40%, alternatively from about 10% to about 30%, alternatively from about 12% to about 25%, alternatively from about 13% to about 23%, alternatively from about 14% to about 21%, alternatively from about 15% to about 20%.

The cleansing composition can include from about 3% to about 30% anionic surfactant, alternatively from about 4% to about 20%, alternatively from about 5% to about 15%, alternatively from about 6% to about 12%, and alternatively from about 7% to about 10%. The cleansing composition can include from about 3% to about 40% amphoteric surfactant, alternatively from about 4% to about 30%, alternatively from about 5% to about 25%, alternatively from about 6% to about 18%, alternatively from about 7% to about 15%, alternatively from about 8% to about 13%, and alternatively from about 9% to about 11%.

The ratio of anionic surfactant to amphoteric surfactant can be from about 0.25:1 to about 3:1, alternatively from about 0.3:1 to about 2.5:1, alternatively from about 0.4:1 to about 2:1, alternatively from about 0.5:1 to about 1.5:1, alternatively from about 0.6:1 to about 1.25:1, and alternatively from about 0.75:1 to about 1:1. The ratio of anionic surfactant to amphoteric surfactant can be from about 0.4:1 to about 1.25:1, alternatively from about 0.5:1 to about 1.1:1, and alternatively from about 0.6:1 to about 1:1. In some examples, the ratio of anionic surfactant to amphoteric surfactant is less than 2:1, alternatively less than 1.75:1, alternatively less than 1.5:1, alternatively less than 1.1:1, and alternatively less than 1:1.

In some examples, inorganic salt is added to the shampoo composition with the surfactant raw materials. In one example, the surfactant raw materials include less than 1.5% inorganic salt, alternatively less than 1.25%, alternatively less than 1%, alternatively less than 0.7%, alternatively less than 0.5%, alternatively less than 0.25%, alternatively less than 0.2%, alternatively less than 0.15%, alternatively less than or equal to 0.1%. In some examples, at least 0.05% inorganic salt is added to the formula via the surfactant raw materials, alternatively at least 0.07%, and alternatively at least 0.1%.

The surfactant system can include one or more amino acid based anionic surfactants. Non-limiting examples of amino acid based anionic surfactants can include sodium, ammonium or potassium salts of acyl glycinates; sodium, ammonium or potassium salts of acyl sarcosinates; sodium, ammonium or potassium salts of acyl glutamates; sodium, ammonium or potassium salts of acyl alaninates and combinations thereof.

The amino acid based anionic surfactant can be a glutamate, for instance an acyl glutamate. Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The amino acid based anionic surfactant can be an alaninate, for instance an acyl alaninate. Non-limiting example of acyl alaninates can include sodium cocoyl alaninate, sodium lauroyl alaninate, sodium N-dodecanoyl-l-alaninate and combination thereof.

The amino acid based anionic surfactant can be a sarcosinate, for instance an acyl sarcosinate. Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

The amino acid based anionic surfactant can be a glycinate for instance an acyl glycinate. Non-limiting example of acyl glycinates can include sodium cocoyl glycinate, sodium lauroyl glycinate and combination thereof.

The composition can contain additional anionic surfactants selected from the group consisting of sulfosuccinates, isethionates, sulfonates, sulfoacetates, glucose carboxylates, alkyl ether carboxylates, acyl taurates, and mixture thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof. The composition can comprise a sulfosuccinate level from about 2% to about 22%, by weight, from about 3% to about 19%, by weight, 4% to about 17%, by weight, and/or from about 5% to about 15%, by weight. Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sulfonates can include alpha olefin sulfonates, linear alkylbenzene sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of acyl taurates can include sodium methyl cocoyl taurate, sodium methyl lauroyl taurate, sodium methyl oleoyl taurate, sodium caproyl methyltaurate and combination thereof.

The surfactant system may further comprise one or more amphoteric surfactants and the amphoteric surfactant can be selected from the group consisting of betaines, sultaines, hydroxysultanes, amphohydroxypropyl sulfonates, alkyl amphoactates, alkyl amphodiacetates, alkyl amphopropionates and combination thereof.

Examples of betaine amphoteric surfactants can include coco dimethyl carboxymethyl betaine, cocoamidopropyl betaine (CAPB), cocobetaine, lauryl amidopropyl betaine (LAPB), oleyl betaine, coco-betaine, cetyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Non-limiting example of alkylamphoacetates can include sodium cocoyl amphoacetate, sodium lauroyl amphoacetate and combination thereof.

The amphoteric surfactant can comprise cocamidopropyl betaine (CAPB), lauramidopropyl betaine (LAPB), and combinations thereof.

The surfactant system may further comprise one or more non-ionic surfactants and the non-ionic surfactant can be selected from the group consisting alkyl polyglucoside, alkyl glycoside, acyl glucamide and mixture thereof. Non-limiting examples of alkyl polyglucosides can include decyl glucoside, cocoyl glucoside, lauroyl glucoside and combination thereof.

Non-limiting examples of acyl glucamide can include lauroyl/myristoyl methyl glucamide, capryloyl/caproyl methyl glucamide, lauroyl/myristoyl methyl glucamide, cocoyl methyl glucamide and combinations thereof.

The composition can contain a non-ionic detersive surfactants that can include cocamide, cocamide methyl MEA, cocamide DEA, cocamide MEA, cocamide MIPA, lauramide DEA, lauramide MEA, lauramide MIPA, myristamide DEA, myristamide MEA, PEG-20 cocamide MEA, PEG-2 cocamide, PEG-3 cocamide, PEG-4 cocamide, PEG-5 cocamide, PEG-6 cocamide, PEG-7 cocamide, PEG-3 lauramide, PEG-5 lauramide, PEG-3 oleamide, PPG-2 cocamide, PPG-2 hydroxyethyl cocamide, and mixtures thereof.

Sclerotium Gum

The shampoo composition comprises 0.15 wt % to 1.05 wt % sclerotium gum, 0.15 wt % to 1.0 wt % sclerotium gum, 0.2 wt % to 0.8 wt % sclerotium gum, 0.4 wt % to 0.8 wt % sclerotium gum, and/or 0.4 wt % to 0.6 wt % sclerotium gum, and any combination thereof. Sclerotium gum is also called scleroglucan, and it is a branched polysaccharide. In some instances, the primary structure of the scleroglucan consists of glucose molecules linked by $\beta$-(1,3) linkage, and every third glucose molecule in the primary structure contains an additional glucose molecule linked by a $\beta$-(1,6) linkage. In certain solutions, scleroglucan forms a triple helix shape.

Figure 2:
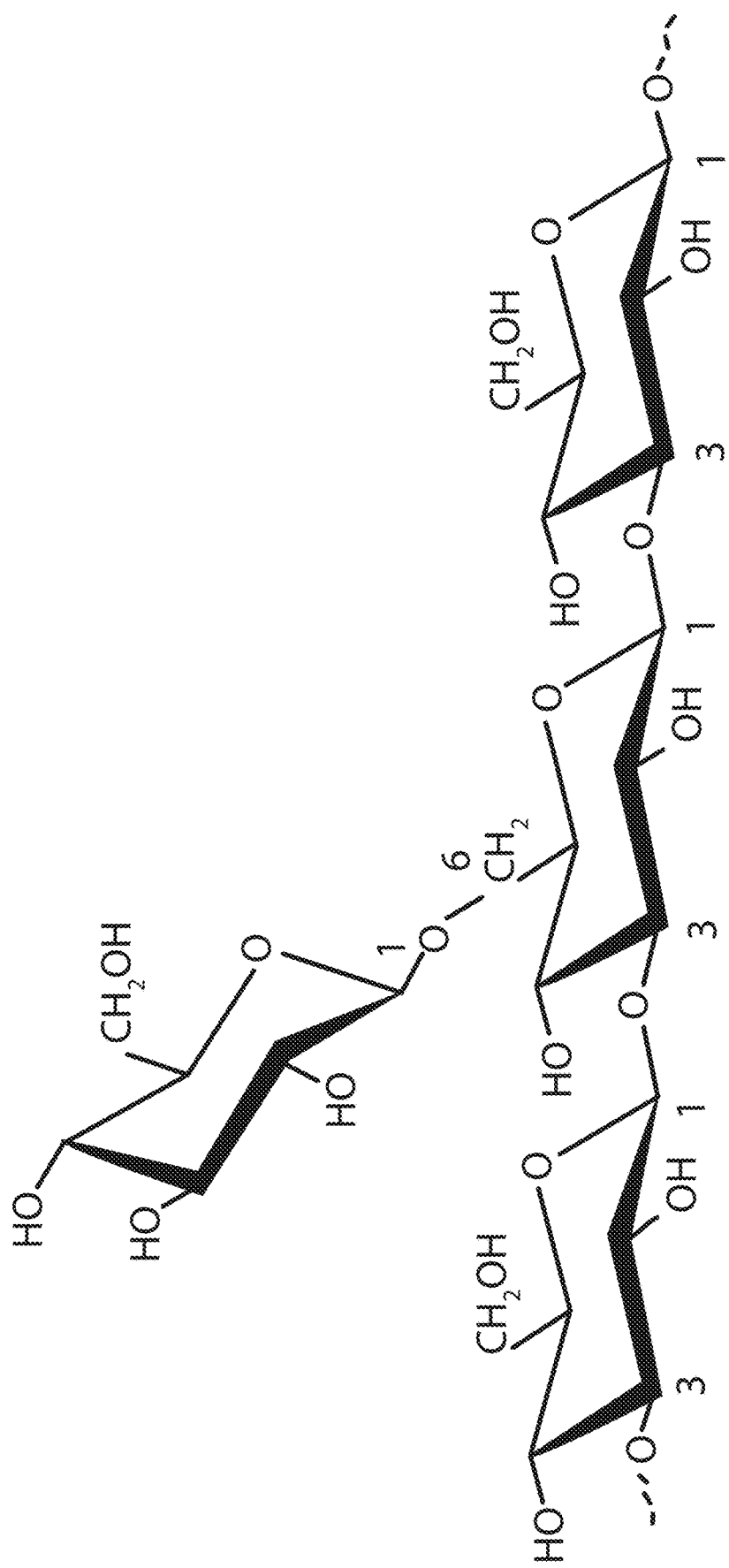
FIG. 2 shows a β-(1,3)-β-(1,6) glucan structure.
Figure 3:
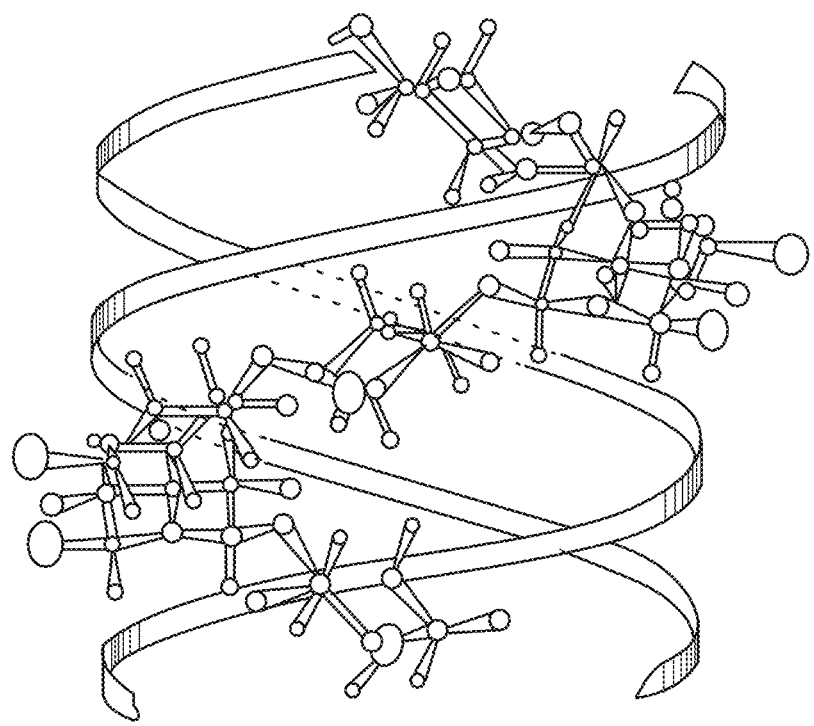
FIG. 3 shows a tridimensional conformation of scleroglucan triplex.

FIG. 1 shows an example of a typical sclerotium gum structure. FIG. 2 shows an example of a $\beta$-(1,3)-$\beta$-(1,6) glucan structure exhibiting the (3:1) side branching ratio of scleroglucan (Martin et al., 2007). FIG. 3 shows an example of a tridimensional conformation of a scleroglucan triplex (Crescenzi et al., 1988). Specific examples of sclerotium gum include Amigum ER commercially available from Alban Muller, Actigum CS 11 QD commercially available from Cargill.

Cationic Polymer

A cleansing composition can include a cationic polymer to allow formation of a coacervate. As can be appreciated, the cationic charge of a cationic polymer can interact with an anionic charge of a surfactant to form the coacervate. Suitable cationic polymers can include: (a) a cationic guar polymer, (b) a cationic non-guar galactomannan polymer, (c) a cationic starch polymer, (d) a cationic copolymer of acrylamide monomers and cationic monomers, (e) a synthetic, non-crosslinked, cationic polymer, which may or may not form lyotropic liquid crystals upon combination with the detersive surfactant, and (f) a cationic cellulose polymer. In certain examples, more than one cationic polymer can be included.

A cationic polymer can be included by weight of the cleansing composition at about 0.05% to about 3%, about 0.075% to about 2.0%, or at about 0.1% to about 1.0%. Cationic polymers can have cationic charge densities of about 0.6 meq/g or more, of about 0.9 meq/g or more, about 1.2 meq/g or more, and about 1.5 meq/g or more. However, cationic charge density can also be about 7 meq/g or less and alternatively about 5 meq/g or less. Cationic polymers can have cationic charge densities of from about 0.2 meq/g to about 2.2 meq/g, from about 0.3 meq/g to about 2.0 meq/g, from about 0.4 meq/g to about 1.8 meq/g; from about 0.5 meq/g to about 1.7 meq/g and from about 0.6 meq/g to about 1.3. In some examples the composition can include a cationic polymer with charge density of about 1.7 to about 2.1 meq/g and about 1 to about 1.5% total inorganic salt. The charge densities can be measured at the pH of intended use of the cleansing composition. (e.g., at about pH 3 to about pH 9; or about pH 4 to about pH 8). The average molecular weight of cationic polymers can generally be between about 10,000 and 10 million, between about 50,000 and about 5 million, and between about 100,000 and about 3 million, and between about 300,000 and about 3 million and between about 100,000 and about 2.5 million. Low molecular weight cationic polymers can be used. Low molecular weight cationic polymers can have greater translucency in the liquid carrier of a cleansing composition. The cationic polymer can be a single type, such as the cationic guar polymer guar hydroxypropyltrimonium chloride having a weight average molecular weight of about 2.5 million g/mol or less, and the cleansing composition can have an additional cationic polymer of the same or different types.

Charge density of cationic polymers other than cationic guar polymers can be determined by measuring % Nitrogen. % Nitrogen is measured using USP <461> Method II. % Nitrogen can then be converted to Cationic Polymer Charge Density by calculations known in the art.

The charge density of cationic guar polymers can be calculated as follows: first, calculate the degree of substitution, as disclosed in WO 2019/096601, page 3, lines 4-22, and then cationic charge density can be calculated from the degree of substitution, as described in WO 2013/011122, page 8, lines 8-17, the disclosure of these publications are incorporated by reference.

Cationic Guar Polymer

The cationic polymer can be a cationic guar polymer, which is a cationically substituted galactomannan (guar) gum derivative. Suitable guar gums for guar gum derivatives can be obtained as a naturally occurring material from the seeds of the guar plant. As can be appreciated, the guar molecule is a straight chain mannan which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums can be obtained through reactions between the hydroxyl groups of the polygalactomannan and reactive quaternary ammonium compounds. The degree of substitution of the cationic groups onto the guar structure can be sufficient to provide the requisite cationic charge density described above.

A cationic guar polymer can have a weight average molecular weight ("M.Wt.") of less than about 3 million g/mol, and can have a charge density from about 0.05 meq/g to about 2.5 meq/g. Alternatively, the cationic guar polymer can have a weight average M.Wt. of less than 1.5 million g/mol, from about 150 thousand g/mol to about 1.5 million g/mol, from about 200 thousand g/mol to about 1.5 million g/mol, from about 300 thousand g/mol to about 1.5 million g/mol, and from about 700,000 thousand g/mol to about 1.5 million g/mol. The cationic guar polymer can have a charge density from about 0.2 meq/g to about 2.2 meq/g, from about 0.3 meq/g to about 2.0 meq/g, from about 0.4 meq/g to about 1.8 meq/g, from about 0.5 meq/g to about 1.7 meq/g, and from about 0.6 meq/g to about 1.3 meq/g.

A cationic guar polymer can have a weight average M.Wt. of less than about 1 million g/mol, and can have a charge density from about 0.1 meq/g to about 2.5 meq/g. A cationic guar polymer can have a weight average M.Wt. of less than 900 thousand g/mol, from about 150 thousand to about 800 thousand g/mol, from about 200 thousand g/mol to about 700 thousand g/mol, from about 300 thousand to about 700 thousand g/mol, from about 400 thousand to about 600 thousand g/mol, from about 150 thousand g/mol to about 800 thousand g/mol, from about 200 thousand g/mol to about 700 thousand g/mol, from about 300 thousand g/mol to about 700 thousand g/mol, and from about 400 thousand g/mol to about 600 thousand g/mol. A cationic guar polymer has a charge density from about 0.2 meq/g to about 2.2 meq/g, from about 0.3 meq/g to about 2.0 meq/g, from about 0.4 meq/g to about 1.8 meq/g; and from about 0.5 meq/g to about 1.5 meq/g.

A cleansing composition can include from about 0.01% to less than about 0.7%, by weight of the cleansing composition of a cationic guar polymer, from about 0.04% to about 0.55%, by weight, from about 0.08% to about 0.5%, by weight, from about 0.16% to about 0.5%, by weight, from about 0.2% to about 0.5%, by weight, from about 0.3% to about 0.5%, by weight, and from about 0.4% to about 0.5%, by weight.

The cationic guar polymer can be formed from quaternary ammonium compounds which conform to general Formula II:

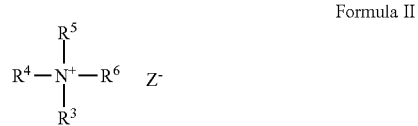

Formula II wherein where $R^3$, $R^4$ and $R^5$ are methyl or ethyl groups; and $R^6$ is either an epoxyalkyl group of the general Formula III:

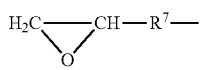

Formula III or $R^6$ is a halohydrin group of the general Formula IV:

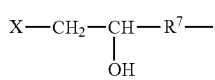

Formula IV wherein $R^7$ is a $C_1$ to $C_3$ alkylene; X is chlorine or bromine, and Z is an anion such as Cl—, Br—, I— or $HSO_4$—. Suitable cationic guar polymers can conform to the general formula V:

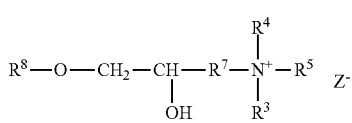

Formula V wherein $R^8$ is guar gum; and wherein $R^4$, $R^5$, $R^6$ and $R^7$ are as defined above; and wherein Z is a halogen. Suitable cationic guar polymers can conform to Formula VI:

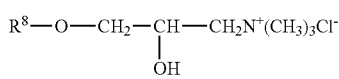

Formula VI wherein $R^8$ is guar gum.

Suitable cationic guar polymers can also include cationic guar gum derivatives, such as guar hydroxypropyltrimonium chloride. Suitable examples of guar hydroxypropyltrimonium chlorides can include the Jaguar series commercially available from Solvay® S.A., Hi-Care Series from Rhodia®, and N-Hance™ and AquaCat™ from Ashland™ Inc. For example, N-Hance™ BF-17 is a borate (boron) free guar polymers. N-Hance™ BF-17 has a charge density of about 1.7 meq/g and M.Wt. of about 800,000. BF-17 has a charge density of about 1.7 meq/g and M.Wt. of about 800,000. BF-17 has a charge density of about 1.7 meq/g and M.Wt. of about 800,000. BF-17 has a charge density of about 1.7 meq/g and M.Wt. of about 800,000. BF-17 has a charge density of about 1.7 meq/g and M.Wt. of about 800,000.

Cationic Non-Guar Galactomannan Polymer

The cationic polymer can be a galactomannan polymer derivative. Suitable galactomannan polymer can have a mannose to galactose ratio of greater than 2:1 on a monomer to monomer basis and can be a cationic galactomannan polymer derivative or an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers can be present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and can be affected by climate. Non Guar Galactomannan polymer derivatives can have a ratio of mannose to galactose of greater than 2:1 on a monomer to monomer basis. Suitable ratios of mannose to galactose can also be greater than 3:1 or greater than 4:1. Analysis of mannose to galactose ratios is well known in the art and is typically based on the measurement of the galactose content.

The gum for use in preparing the non-guar galactomannan polymer derivatives can be obtained from naturally occurring materials such as seeds or beans from plants. Examples of various non-guar galactomannan polymers include Tara gum (3 parts mannose/1 part galactose), Locust bean or Carob (4 parts mannose/1 part galactose), and Cassia gum (5 parts mannose/1 part galactose).

A non-guar galactomannan polymer derivative can have a M. Wt. from about 1,000 g/mol to about 10,000,000 g/mol, and a M.Wt. from about 5,000 g/mol to about 3,000,000 g/mol.

The cleansing compositions described herein can include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure can be sufficient to provide the requisite cationic charge density.

A galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general Formulas II to VI, as defined above.

Cationic non-guar galactomannan polymer derivatives formed from the reagents described above can be represented by the general Formula VII:

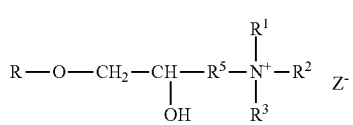

Formula VII wherein R is the gum. The cationic galactomannan derivative can be a gum hydroxypropyltrimethylammonium chloride, which can be more specifically represented by the general Formula VIII:

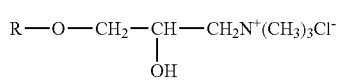

Formula VIII

The galactomannan polymer derivative can be an amphoteric galactomannan polymer derivative having a net positive charge, obtained when the cationic galactomannan polymer derivative further comprises an anionic group.

A cationic non-guar galactomannan can have a ratio of mannose to galactose which is greater than 4:1, a M.Wt. of about 100,000 g/mol to about 500,000 g/mol, a M.Wt. of about 50,000 g/mol to about 400,000 g/mol, and a cationic charge density from about 1 meq/g to about 5 meq/g, and from about 2 meq/g to about 4 meq/g.

Cleansing compositions can include at least about 0.05% of a galactomannan polymer derivative by weight of the composition. The cleansing compositions can include from about 0.05% to about 2%, by weight of the composition, of a galactomannan polymer derivative.

Cationic Starch Polymers

Suitable cationic polymers can also be water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The cleansing compositions described herein can include cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers can have a molecular weight from about 850,000 g/mol to about 15,000,000 g/mol and from about 900,000 g/mol to about 5,000,000 g/mol.

Cationically modified starch polymers can have a charge density of from about 0.2 meq/g to about 5 meq/g, and from about 0.2 meq/g to about 2 meq/g. The chemical modification to obtain such a charge density can include the addition of amino and/or ammonium groups into the starch molecules. Non-limiting examples of such ammonium groups can include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. Further details are described in Solarek, D. B., Cationic Starches in Modified Starches: Properties and Uses, Wurzburg, O. B., Ed., CRC Press, Inc., Boca Raton, Fla. 1986, pp 113-125 which is hereby incorporated by reference. The cationic groups can be added to the starch prior to degradation to a smaller molecular weight or the cationic groups may be added after such modification.

A cationically modified starch polymer can have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution can be determined using proton nuclear magnetic resonance spectroscopy ("$^1$H NMR") methods well known in the art. Suitable $^1$H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be selected from a variety of sources such as tubers, legumes, cereal, and grains. For example, starch sources can include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof. Suitable cationically modified starch polymers can be selected from degraded cationic maize starch, cationic tapioca, cationic potato starch, and mixtures thereof. Cationically modified starch polymers are cationic corn starch and cationic tapioca.

The starch, prior to degradation or after modification to a smaller molecular weight, can include one or more additional modifications. For example, these modifications may include cross-linking, stabilization reactions, phosphorylations, and hydrolyzations. Stabilization reactions can include alkylation and esterification.

Cationically modified starch polymers can be included in a cleansing composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

The starch can be readily soluble in water and can form a substantially translucent solution in water. The transparency of the composition is measured by Ultra-Violet/Visible ("UV/VIS") spectrophotometry, which determines the absorption or transmission of UV/VIS light by a sample, using a Gretag Macbeth Colorimeter Color. A light wavelength of 600 nm has been shown to be adequate for characterizing the degree of clarity of cleansing compositions.

Cationic Copolymer of an Acrylamide Monomer and a Cationic Monomer

A cleansing composition can include a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

Suitable cationic polymers can include:
(i) an acrylamide monomer of the following Formula IX:

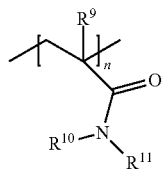

Formula IX where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$ cycloalkyl; and (ii) a cationic monomer conforming to Formula X:

Formula X

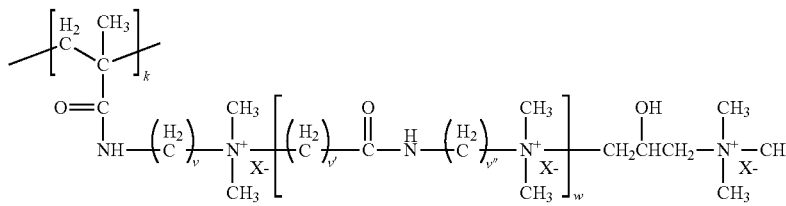

where k=1, each of v, v', and v" is independently an integer of from 1 to 6, w is zero or an integer of from 1 to 10, and X⁻ is an anion.

A cationic monomer can conform to Formula X where k=1, v=3 and w=0, z=1 and X⁻ is Cl⁻ to form the following structure (Formula XI):

Formula XI

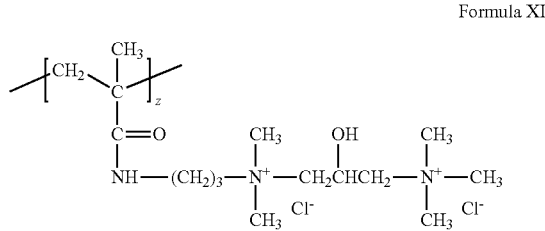

As can be appreciated, the above structure can be referred to as diquat.

A cationic monomer can conform to Formula X wherein v and v" are each 3, v'=1, w=1, y=1 and X⁻ is Cl⁻, to form the following structure of Formula XII:

Formula XII

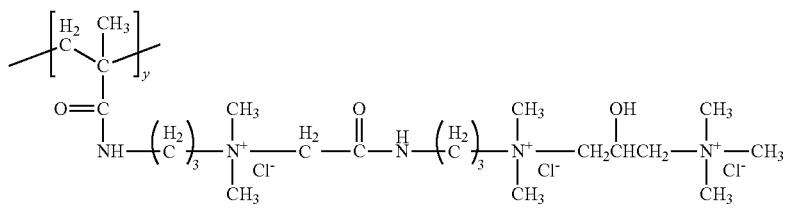

The structure of Formula XII can be referred to as triquat.

The acrylamide monomer can be either acrylamide or methacrylamide.

The cationic copolymer can be AM:TRIQUAT which is a copolymer of acrylamide and 1,3-Propanediaminium,N-[2-[[[dimethyl[3-[(2-methyl-1-oxo-2-propenyl)amino]propyl [ammonio[acetyl]amino]ethyl]2-hydroxy-N,N,N',N'-pentamethyl-, trichloride. AM:TRIQUAT is also known as polyquaternium 76 (PQ76). AM:TRIQUAT can have a charge density of 1.6 meq/g and a M.Wt. of 1.1 million g/mol.

The cationic copolymer can include an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminoethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can include a cationic monomer selected from the group consisting of: trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters can be cationized esters of the (meth)acrylic acid containing a quaternized N atom. Cationized esters of the (meth)acrylic acid containing a quaternized N atom can be quaternized dialkylaminoalkyl (meth)acrylates with $C_1$ to $C_3$ in the alkyl and alkylene groups. The cationized esters of the (meth)acrylic acid containing a quaternized N atom can be selected from the group consisting of ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth) acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides are quaternized dialky laminoalkyl(meth)acrylamides with $C_1$ to $C_3$ in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide can be a quaternized dialkylaminoalkyl(meth)acrylamide with $C_1$ to $C_3$ in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate. The cationic monomer can be a hydrolysis-stable cationic monomer. Hydrolysis-stable cationic monomers can be, in addition to a dialkylaminoalkyl(meth)acrylamide, any monomer that can be regarded as stable to the OECD hydrolysis test. The cationic monomer can be hydrolysis-stable, and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, from about 1.1 meq/g to about 2.3 meq/g, from about 1.2 meq/g to about 2.2 meq/g, from about 1.2 meq/g to about 2.1 meq/g, from about 1.3 meq/g to about 2.0 meq/g, and from about 1.3 meq/g to about 1.9 meq/g.

The cationic copolymer can have a M.Wt. from about 100 thousand g/mol to about 2 million g/mol, from about 300 thousand g/mol to about 1.8 million g/mol, from about 500 thousand g/mol to about 1.6 million g/mol, from about 700 thousand g/mol to about 1.4 million g/mol, and from about 900 thousand g/mol to about 1.2 million g/mol.

The cationic copolymer can be a trimethylammoniopropylmethacrylamide chloride-N-Acrylamide copolymer, which is also known as AM:MAPTAC. AM:MAPTAC can have a charge density of about 1.3 meq/g and a M.Wt. of about 1.1 million g/mol. The cationic copolymer can be AM:ATPAC. AM:ATPAC can have a charge density of about 1.8 meq/g and a M.Wt. of about 1.1 million g/mol.

Synthetic Polymers

A cationic polymer can be a synthetic polymer that is formed from:

i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers which have the structure of Formula XIII:

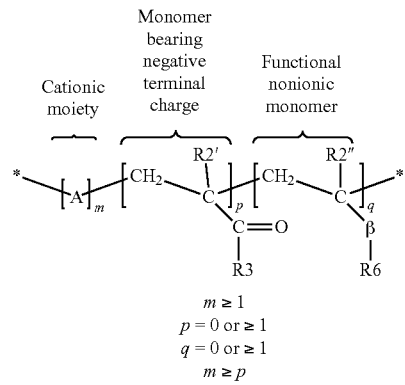

where A, may be one or more of the following cationic moieties:

where @=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl arylox;

where Z=C1-C22 alkyl, alkyloxy, aryl or aryloxy;

where R1=H, C1-C4 linear or branched alkyl;

where s=0 or 1, n=0 or ≥1;

where T and R7=C1-C22 alkyl; and where X−=halogen, hydroxide, alkoxide, sulfate or alkylsulfate.

Where the monomer bearing a negative charge is defined by R2'=H, $C_1$-$C_4$ linear or branched alkyl and R3 is:

-continued

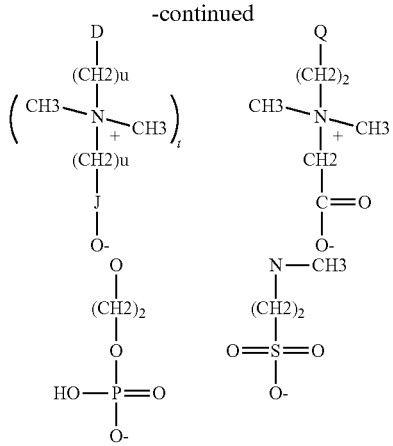

where D=O, N, or S;
where Q=NH$_2$ or O;
where u=1-6;
where t=0-1; and
where J=oxygenated functional group containing the following elements P, S, C.

Where the nonionic monomer is defined by R2"=H, C$_1$-C$_4$ linear or branched alkyl, R6=linear or branched alkyl, alkyl aryl, aryl oxy, alkyloxy, alkylaryl oxy and β is defined as

and
where G' and G" are, independently of one another, O, S or N—H and L=0 or 1.

Suitable monomers can include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of suitable cationic monomers can include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers can include quaternary monomers of formula —NR$_3^+$, wherein each R can be identical or different, and can be a hydrogen atom, an alkyl group comprising 1 to 10 carbon atoms, or a benzyl group, optionally carrying a hydroxyl group, and including an anion (counter-ion). Examples of suitable anions include halides such as chlorides, bromides, sulphates, hydrosulphates, alkylsulphates (for example comprising 1 to 6 carbon atoms), phosphates, citrates, formates, and acetates.

Suitable cationic monomers can also include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Additional suitable cationic monomers can include trimethyl ammonium propyl (meth) acrylamido chloride.

Examples of monomers bearing a negative charge include alpha ethylenically unsaturated monomers including a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge can include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers can include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds. Suitable nonionic monomers can also include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethylhexyl acrylate, 2-ethyl-hexyl methacrylate, 2-hydroxyethylacrylate and 2-hydroxyethylmethacrylate.

The anionic counterion (X$^-$) in association with the synthetic cationic polymers can be any known counterion so long as the polymers remain soluble or dispersible in water, in the cleansing composition, or in a coacervate phase of the cleansing composition, and so long as the counterions are physically and chemically compatible with the essential components of the cleansing composition or do not otherwise unduly impair product performance, stability or aesthetics. Non limiting examples of suitable counterions can include halides (e.g., chlorine, fluorine, bromine, iodine), sulfate, and methylsulfate.

The cationic polymer described herein can also aid in repairing damaged hair, particularly chemically treated hair by providing a surrogate hydrophobic F-layer. The microscopically thin F-layer provides natural weatherproofing, while helping to seal in moisture and prevent further damage. Chemical treatments damage the hair cuticle and strip away its protective F-layer. As the F-layer is stripped away, the hair becomes increasingly hydrophilic. It has been found that when lyotropic liquid crystals are applied to chemically treated hair, the hair becomes more hydrophobic and more virgin-like, in both look and feel. Without being limited to any theory, it is believed that the lyotropic liquid crystal complex creates a hydrophobic layer or film, which coats the hair fibers and protects the hair, much like the natural F-layer protects the hair. The hydrophobic layer can return the hair to a generally virgin-like, healthier state. Lyotropic liquid crystals are formed by combining the synthetic cationic polymers described herein with the aforementioned anionic detersive surfactant component of the cleansing composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in PCT Patent App. No. WO 94/06403 which is incorporated by reference. The synthetic polymers described herein can be formulated in a stable cleansing composition that provides improved conditioning performance, with respect to damaged hair.

Cationic synthetic polymers that can form lyotropic liquid crystals have a cationic charge density of from about 2 meq/gm to about 7 meq/gm, and/or from about 3 meq/gm to about 7 meq/gm, and/or from about 4 meq/gm to about 7 meq/gm. The cationic charge density is about 6.2 meq/gm. The polymers also have a M. Wt. of from about 1,000 to about 5,000,000, and/or from about 10,000 to about 2,000,000, and/or from about 100,000 to about 2,000,000.

Cationic synthetic polymers that provide enhanced conditioning and deposition of benefit agents but do not necessarily form lytropic liquid crystals can have a cationic charge density of from about 0.7 meq/gm to about 7 meq/gm, and/or from about 0.8 meq/gm to about 5 meq/gm, and/or from about 1.0 meq/gm to about 3 meq/gm. The polymers also have a M.Wt. of from about 1,000 g/mol to about 5,000,000 g/mol, from about 10,000 g/mol to about 2,000,000 g/mol, and from about 100,000 g/mol to about 2,000,000 g/mol.

Cationic Cellulose Polymer

Suitable cationic polymers can be cellulose polymers. Suitable cellulose polymers can include salts of hydroxyethyl cellulose reacted with trimethyl ammonium substituted epoxide, referred to in the industry (CTFA) as Polyquaternium 10 and available from Dwo/Amerchol Corp. (Edison, N.J., USA) in their Polymer LR, JR, and KG series of polymers. Other suitable types of cationic cellulose can include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose can include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H. Cationic cellulose polymers can have a cationic charge density of from about 0.2 meq/g to about 2.2 meq/g, from about 0.3 meq/g to about 2.0 meq/g, from about 0.4 meq/g to about 1.8 meq/g; from about 0.5 meq/g to about 1.7 meq/g and from about 0.6 meq/g to about 1.3.

Additional cationic polymers are also described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which is incorporated herein by reference. Techniques for analysis of formation of complex coacervates are known in the art. For example, microscopic analyses of the compositions, at any chosen stage of dilution, can be utilized to identify whether a coacervate phase has formed. Such coacervate phase can be identifiable as an additional emulsified phase in the composition. The use of dyes can aid in distinguishing the coacervate phase from other insoluble phases dispersed in the composition. Additional details about the use of cationic polymers and coacervates are disclosed in U.S. Pat. No. 9,272,164 which is incorporated by reference.

Liquid Carrier

As can be appreciated, cleansing compositions can desirably be in the form of pourable liquid under ambient conditions. Inclusion of an appropriate quantity of a liquid carrier can facilitate the formation of a cleansing composition having an appropriate viscosity and rheology. A cleansing composition can include, by weight of the composition, about 20% to about 95%, by weight, of a liquid carrier, and about 60% to about 85%, by weight, of a liquid carrier. The liquid carrier can be an aqueous carrier such as water.

Optional Components

As can be appreciated, cleansing compositions described herein can include a variety of optional components to tailor the properties and characteristics of the composition. As can be appreciated, suitable optional components are well known and can generally include any components which are physically and chemically compatible with the essential components of the cleansing compositions described herein. Optional components should not otherwise unduly impair product stability, aesthetics, or performance. Individual concentrations of optional components can generally range from about 0.001% to about 10%, by weight of a cleansing composition. Optional components can be further limited to components which will not impair the clarity of a translucent cleansing composition.

Suitable optional components which can be included in a cleansing composition can include co-surfactants, deposition aids, conditioning agents (including hydrocarbon oils, fatty esters, silicones), anti-dandruff agents, suspending agents, viscosity modifiers, dyes, nonvolatile solvents or diluents (water soluble and insoluble), pearlescent aids, foam boosters, pediculocides, pH adjusting agents, perfumes, preservatives, chelants, proteins, skin active agents, sunscreens, UV absorbers, and vitamins. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to the composition herein.

Conditioning Agents

A cleansing composition can include a silicone conditioning agent. Suitable silicone conditioning agents can include volatile silicone, non-volatile silicone, or combinations thereof. If including a silicone conditioning agent, the agent can be included from about 0.01% to about 10%, by weight of the composition, from about 0.1% to about 8%, from about 0.1% to about 5%, and/or from about 0.2% to about 3%. Examples of suitable silicone conditioning agents, and optional suspending agents for the silicone, are described in U.S. Reissue Pat. No. 34,584, U.S. Pat. Nos. 5,104,646, and 5,106,609, each of which is incorporated by reference herein. Suitable silicone conditioning agents can have a viscosity, as measured at 25° C., from about 20 centistokes ("csk") to about 2,000,000 csk, from about 1,000 csk to about 1,800,000 csk, from about 50,000 csk to about 1,500,000 csk, and from about 100,000 csk to about 1,500,000 csk.

The dispersed silicone conditioning agent particles can have a volume average particle diameter ranging from about 0.01 micrometer to about 50 micrometer. For small particle application to hair, the volume average particle diameters can range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), which is incorporated herein by reference.

Silicone emulsions suitable for the cleansing compositions described herein can include emulsions of insoluble polysiloxanes prepared in accordance with the descriptions provided in U.S. Pat. No. 4,476,282 and U.S. Patent Application Publication No. 2007/0276087 each of which is incorporated herein by reference. Suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

Other classes of silicones suitable for the cleansing compositions described herein can include i) silicone fluids, including silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Alternatively, the cleansing composition can be substantially free or free of silicones.

Organic Conditioning Materials

The conditioning agent of the cleansing compositions described herein can also include at least one organic conditioning material such as oil or wax, either alone or in combination with other conditioning agents, such as the silicones described above. The organic material can be non-polymeric, oligomeric or polymeric. The organic material can be in the form of an oil or wax and can be added in the cleansing formulation neat or in a pre-emulsified form. Suitable examples of organic conditioning materials can include: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Emulsifiers

A variety of anionic and nonionic emulsifiers can be used in the cleansing composition of the present invention. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

The cleansing composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term includes alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. Nos. 5,747,440, and 5,747,440 are each incorporated by reference herein. Suitable chelants can further include histidine.

Levels of an EDDS chelant or histidine chelant in the cleansing compositions can be low. For example, an EDDS chelant or histidine chelant can be included at about 0.01%, by weight. Above about 10% by weight, formulation and/or human safety concerns can arise. The level of an EDDS chelant or histidine chelant can be at least about 0.01%, by weight, at least about 0.05%, by weight, at least about 0.1%, by weight, at least about 0.25%, by weight, at least about 0.5%, by weight, at least about 1%, by weight, or at least about 2%, by weight, by weight of the cleansing composition.

Gel Network

A cleansing composition can also include a fatty alcohol gel network. Gel networks are formed by combining fatty alcohols and surfactants in the ratio of from about 1:1 to about 40:1, from about 2:1 to about 20:1, and/or from about 3:1 to about 10:1. The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. Gel networks can provide a number of benefits to cleansing compositions. For example, a gel network can provide a stabilizing benefit to cosmetic creams and hair conditioners. In addition, gel networks can provide conditioned feel benefits to hair conditioners and shampoos.

A fatty alcohol can be included in the gel network at a level by weight of from about 0.05%, by weight, to about 14%, by weight. For example, the fatty alcohol can be included in an amount ranging from about 1%, by weight, to about 10%, by weight, and/or from about 6%, by weight, to about 8%, by weight.

Suitable fatty alcohols include those having from about 10 to about 40 carbon atoms, from about 12 to about 22 carbon atoms, from about 16 to about 22 carbon atoms, and/or about 16 to about 18 carbon atoms. These fatty alcohols can be straight or branched chain alcohols and can be saturated or unsaturated. Nonlimiting examples of fatty alcohols include cetyl alcohol, stearyl alcohol, behenyl alcohol, and mixtures thereof. Mixtures of cetyl and stearyl alcohol in a ratio of from about 20:80 to about 80:20 are suitable.

A gel network can be prepared by charging a vessel with water. The water can then be heated to about 74° C. Cetyl alcohol, stearyl alcohol, and surfactant can then be added to the heated water. After incorporation, the resulting mixture can pass through a heat exchanger where the mixture is cooled to about 35° C. Upon cooling, the fatty alcohols and surfactant crystallized can form crystalline gel network. Table 1 provides the components and their respective amounts for an example gel network composition.

To prepare the gel network pre-mix of Table 1, water is heated to about 74° C. and the fatty alcohol and gel network surfactant are added to it in the quantities depicted in Table 1. After incorporation, this mixture is passed through a mill and heat exchanger where it is cooled to about 32° C. As a result of this cooling step, the fatty alcohol, the gel network surfactant, and the water form a crystalline gel network.

TABLE 1

| Premix | % |
|---|---|
| Gel Network Surfactant[1] | 11.00 |
| Stearyl Alcohol | 8% |
| Cetyl Alcohol | 4% |
| Water | QS |

[1]For anionic gel networks, suitable gel network surfactants above include surfactants with a net negative charge including sulfonates, carboxylates and phosphates among others and mixtures thereof.

For cationic gel networks, suitable gel network surfactants above include surfactants with a net positive charge including quaternary ammonium surfactants and mixtures thereof.

For Amphoteric or Zwitterionic gel networks, suitable gel network surfactants above include surfactants with both a positive and negative charge at product usage pH including betaines, amine oxides, sultaines, amino acids among others and mixtures thereof.

Benefit Agents

A cleansing composition can further include one or more benefit agents. Exemplary benefit agents include, but are not limited to, particles, colorants, perfume microcapsules, gel networks, and other insoluble skin or hair conditioning agents such as skin silicones, natural oils such as sunflower oil or castor oil. The benefit agent can be selected from the group consisting of particles; colorants; perfume microcapsules; gel networks; other insoluble skin or hair conditioning agents such as skin silicones, natural oils such as sunflower oil or castor oil; and mixtures thereof.

Suspending Agent

A cleansing composition can include a suspending agent at concentrations effective for suspending water-insoluble material in dispersed form in the compositions or for modifying the viscosity of the composition. Such concentrations range from about 0.1% to about 10%, and from about 0.3% to about 5.0%, by weight of the compositions. As can be appreciated however, suspending agents may not be necessary when certain glyceride ester crystals are included as certain glyceride ester crystals can act as suitable suspending or structuring agents.

Suitable suspending agents can include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Other suitable suspending agents can include crystalline suspending agents which can be categorized as acyl derivatives, long chain amine oxides, and mixtures thereof. Examples of such suspending agents are described in U.S. Pat. No. 4,741,855, which is incorporated herein by reference. Suitable suspending agents include ethylene glycol esters of fatty acids having from 16 to 22 carbon atoms. The suspending agent can be an ethylene glycol stearates, both mono and distearate, but particularly the distearate containing less than about 7% of the mono stearate. Other suitable suspending agents include alkanol amides of fatty acids, having from about 16 to about 22 carbon atoms, alternatively from about 16 to about 18 carbon atoms, suitable examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters as previously described. Long chain acyl derivatives, ethylene glycol esters of long chain carboxylic acids, long chain amine oxides, and alkanol amides of long chain carboxylic acids can also be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan® Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine Still other suitable suspending agents include di(hydrogenated tallow)phthalic acid amide, and crosslinked maleic anhydride-methyl vinyl ether copolymer.

Viscosity Modifiers

The shampoo composition can be free of or substantially free of viscosity modifiers other than organic salt.

In some examples, the composition can contain a viscosity modifier instead of or in addition to organic salt. Viscosity modifiers can be used to modify the rheology of a cleansing composition. Suitable viscosity modifiers can include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol. Other suitable rheology modifiers can include cross-linked acrylates, cross-linked maleic anhydride co-methylvinylethers, hydrophobically modified associative polymers, and mixtures thereof.

Dispersed Particles

Dispersed particles as known in the art can be included in a cleansing composition. If including such dispersed particles, the particles can be incorporated, by weight of the composition, at levels of about 0.025% or more, about 0.05% or more, about 0.1% or more, about 0.25% or more, and about 0.5% or more. However, the cleansing compositions can also contain, by weight of the composition, about 20% or fewer dispersed particles, about 10% or fewer dispersed particles, about 5% or fewer dispersed particles, about 3% or fewer dispersed particles, and about 2% or fewer dispersed particles.

As can be appreciated, a cleansing composition can include still further optional components. For example, amino acids can be included. Suitable amino acids can include water soluble vitamins such as vitamins B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Anti-dandruff agents can be included. As can be appreciated, the formation of a coacervate can facilitate deposition of the anti-dandruff agent to the scalp.

Suitable anti-dandruff agents can include pyridinethione salts, azoles, selenium sulfide, particulate sulfur, and mixtures thereof. Such anti-dandruff particulate should be physically and chemically compatible with the essential components of the composition, and should not otherwise unduly impair product stability, aesthetics or performance A shampoo composition can include a cationic polymer to enhance deposition of an anti-dandruff active.

An anti-dandruff agent can be a pyridinethione particulate such as a 1-hydroxy-2-pyridinethione salt. The concentration of pyridinethione anti-dandruff particulates can range from about 0.1% to about 4%, about 0.1% to about 3%, and from about 0.3% to about 2% by weight of the composition. Suitable pyridinethione salts include those formed from heavy metals such as zinc, tin, cadmium, magnesium, aluminum and zirconium, particularly suitable is the zinc salt of 1-hydroxy-2-pyridinethione (known as "zinc pyridinethione" or "ZPT"), 1-hydroxy-2-pyridinethione salts in platelet particle form, wherein the particles have an average size of up to about 20 µm, up to about 5 µm, up to about 2.5 µm. Salts formed from other cations, such as sodium, can also be suitable. Pyridinethione anti-dandruff agents are further described in U.S. Pat. Nos. 2,809,971; 3,236,733; 3,753,196; 3,761,418; 4,345,080; 4,323,683; 4,379,753; and 4,470,982, each of which are incorporated herein by reference. It is contemplated that when ZPT is used as the anti-dandruff particulate, that the growth or re-growth of hair may be stimulated or regulated, or both, or that hair loss may be reduced or inhibited, or that hair may appear thicker or fuller.

In addition to the anti-dandruff active selected from polyvalent metal salts of pyrithione, a shampoo composition can further include one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Suitable anti-microbials can include itraconazole, ketoconazole, selenium sulphide and coal tar.

A suitable anti-microbial agent can be one material or a mixture selected from: azoles, such as climbazole, ketoconazole, itraconazole, econazole, and elubiol; hydroxy pyridones, such as piroctone olamine, ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline. Examples of azole anti-microbials can include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in a shampoo composition, the soluble anti-microbial active can be included in an amount from about 0.01% to about 5%, from about 0.5% to about 6%, from about 0.1% to about 3%, from about 0.1% to about 9%, from about 0.1% to about 1.5%, from about 0.1% to about 2%, and more from about 0.3% to about 2%, by weight of the composition.

Selenium sulfide is a particulate anti-dandruff agent suitable for use as an anti-microbial compositions when included at concentrations of about 0.1% to about 4%, by weight of the composition, from about 0.3% to about 2.5% by weight, and from about 0.5% to about 1.5% by weight. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), less than 10 μm. Selenium sulfide compounds are described, for example, in U.S. Pat. Nos. 2,694,668; 3,152,046; 4,089,945; and 4,885,107, each of which are incorporated herein by reference.

Sulfur can also be used as a particulate anti-microbial/anti-dandruff agent. Effective concentrations of the particulate sulfur are typically from about 1% to about 4%, by weight of the composition, alternatively from about 2% to about 4%.

Keratolytic agents such as salicylic acid can also be included in a shampoo composition described herein.

A cleansing composition can optionally include pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including water soluble components such as those having C. I. Names.

One or more stabilizers and preservatives can be included. For example, one or more of trihydroxystearin, ethylene glycol distearate, citric acid, sodium citrate dihydrate, a preservative such as kathon, sodium chloride, sodium benzoate, sodium salicylate and ethylenediaminetetraacetic acid ("EDTA") can be included to improve the lifespan of a personal care composition. The stabilizer and/or preservative can be used at a level of from about 0.10% to about 2%. Particularly suitable is sodium benzoate at a level of from about 0.10% to about 0.45%. The personal care composition may also include citric acid at a level of from about 0.5% to about 2%. The sodium benzoate and the citric acid can be added to the personal care composition alone or in combination.

Method of Making a Cleansing Composition

A cleansing composition described herein can be formed similarly to known cleansing compositions. For example, the process of making a cleansing composition can include the step of mixing the surfactant, cationic polymer, and liquid carrier together to form a cleansing composition. The sclerotium gum can be incorporated into the composition by dispersing it first in water, at about a 1:80 polymer-to-water ratio respectively, using a high shear milling device (e.g. IKA T25 DS1 Digital Ultra Turrax homogenizer), adjusting the mill speed and mill time to achieve the desired batch viscosity and rheology. The remaining ingredients were then added to complete the batch.

Additional information on sulfate-free surfactants and other ingredients that are suitable for shampoo compositions is found at U.S. Pub. Nos. 2019/0105247 and 2019/0105246, incorporated by reference.

Test Methods

Argentometry Method to Measure Wt % Inorganic Chloride Salts

The weight % of inorganic chloride salt in the composition can be measured using a potentiometric method where the chloride ions in the composition are titrated with silver nitrate. The silver ions react with the chloride ions from the composition to form an insoluble precipitate, silver chloride. The method used an electrode (Mettler Toledeo DM141) that is designed for potentiometric titrations of anions that precipitate with silver. The largest change in the signal occurs at the equivalence point when the amount of added silver ions is equal to the amount of chloride ions in solution. The concentration of silver nitrate solution used should be calibrated using a chloride solution known to one of skill in the art, such as a sodium chloride solution that contains a standard and known amount of sodium chloride to confirm that the results match the known concentration. This type of titration involving a silver ion is known as argentometry and is commonly used to determine the amount of chloride present in a sample.

Methods to Determine Lack of In Situ Coacervate in Composition Prior to Dilution 1. Microscopy Method to Determine Lack of In Situ Coacervate Lack of in situ coacervate can be determined using a microscope. The composition is mixed to homogenize, if needed. Then, the composition is sampled onto a microscope slide and mounted on a microscope, per typical microscopy practices. The sample is viewed at, for example, a 10× or 20× objective. If in situ coacervate is present in the sample, an amorphous, gel-like phase with about 20 nm to about 200 nm particle size can be seen throughout the sample. This amorphous, gel-like phases can be described as gel chunks or globs. In this method, the in situ coacervate is separate from other ingredients that were intentionally added to the formula that form flocks or otherwise appear as particles under microscopy.

Figure 4:
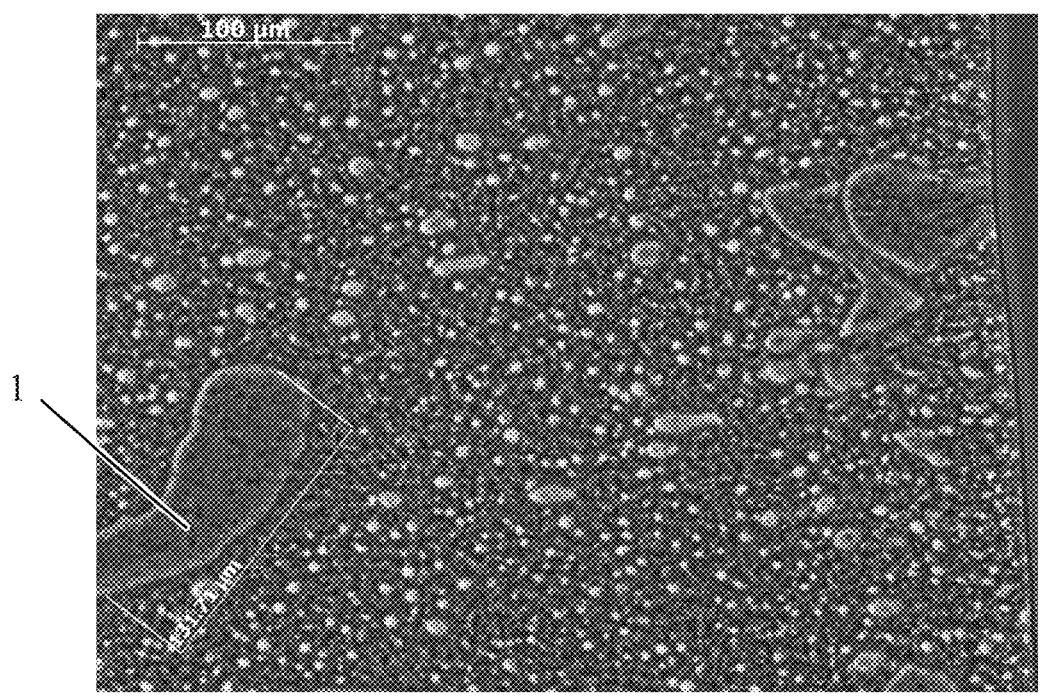
FIG. 4 is a 20× micrograph of a shampoo that contains in situ coacervate.
Figure 5:
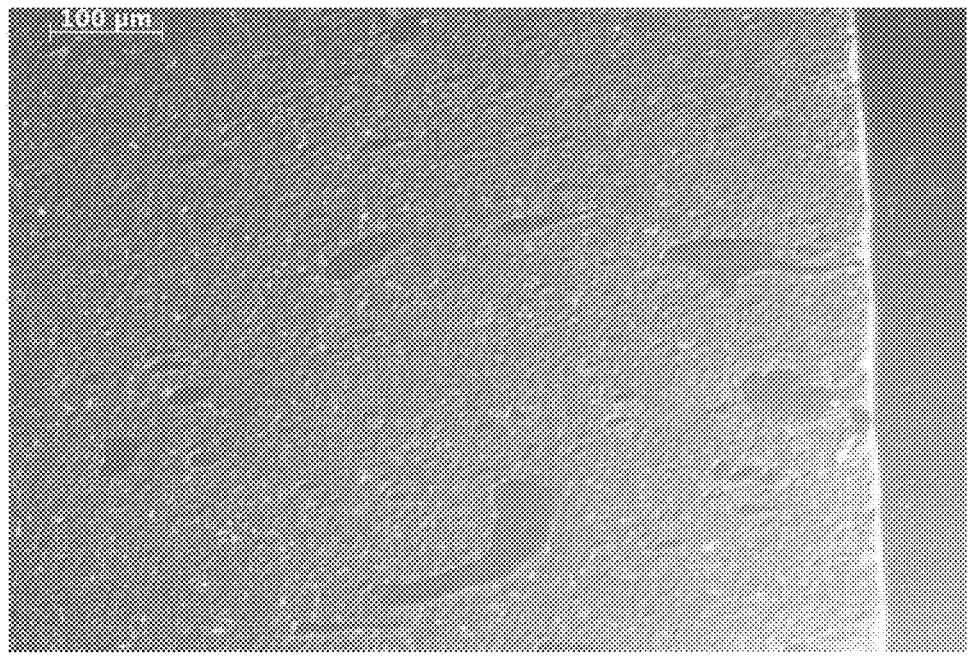
FIG. 5 is 10× micrograph of the shampoo composition of FIG. 1.

FIG. 4 is an example microscopy photograph at 20× objective of a marketed sulfate-free shampoo composition that contains a cationic polymer and also has in situ coacervate. FIG. 4 at reference numeral 1 shows an amorphous, gel-like phase that is about 130 nm long that is the in situ coacervate. FIG. 5 is an example microscopy photograph at 10× objective the same marketed shampoo composition that was used in FIG. 4 at 20× objective. FIG. 5 shows many of these amorphous, gel-like phases present with a length from about 20 nm to about 200 nm.

2. Clarity Assessment—Measurement of % Transmittance (% T)

Lack of in situ coacervate can be determined by composition clarity. A composition that does not contain in situ coacervate will be clear, if it does not contain any ingredients that would otherwise give it a hazy appearance.

Composition clarity can be measured by % Transmittance. For this assessment to determine if the composition lacks coacervate, the composition should be made without ingredients that would give the composition a hazy appearance such as silicones, opacifiers, non-silicone oils, micas, and gums or anionic rheology modifiers. It is believed that adding these ingredients would not cause in situ coacervate to form prior to use, however these ingredients will obscure measurement of clarity by % Transmittance.

Clarity can be measured by % Transmittance (% T) using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to ensure no air bubbles are within the sample before the % T is measured by the spectrophotometer at 600 nm. Alternatively, multiple samples can be measured simultaneously by using a spectrophotometer such as the SpectraMax M-5 available from Molecular Devices. Multiple samples are transferred into a 96 well visible flat bottom plate (Greiner part #655-001), ensuring that no air bubbles are within the samples. The flat bottom plate is placed within the SpectraMax M-5 and % T measured using the Software Pro v.5™ software available from Molecular Devices.

3. Lasentec FBRM Method

Lack of in situ coacervate can also be measured using Lasentec FBRM Method with no dilution. A Lasentec Focused Beam Reflectance Method (FBRM) [model S400A available from Mettler Toledo Corp] may be used to determine floc size and amount as measured by chord length and particle counts/sec (counts per sec).

4. In Situ Coacervate Centrifuge Method

Lack of in situ coacervate can also be measured by centrifuging a composition and measuring in situ coacervate gravimetrically. For this method, the composition should be made without a suspending agent to allow for separation of an in situ coacervate phase. The composition is centrifuged for 20 minutes at 9200 rpm using a Beckman Coulter TJ25 centrifuge. Several time/rpm combinations can be used. The supernatant is then removed and the remaining settled in situ coacervate assessed gravimetrically. % In Situ Coacervate is calculated as the weight of settled in situ coacervate as a percentage of the weight of composition added to the centrifuge tube using the equation below. This quantifies the percentage of the composition that participates in the in situ coacervate phase.

$$\% \text{ In Situ Coacervate} = \frac{\text{Weight of settled in situ coacervate}}{\text{Weight of composition added to centrifuge tube}} \times 100$$

Measures of Improved Performance Due to No In Situ Coacervate Prior to Dilution

The composition does not contain in situ coacervate prior to dilution. Because of this, coacervate quantity and quality upon dilution is better than a composition that does contain in situ coacervate prior to dilution. This provides better wet conditioning and deposition of actives from a composition that does not contain coacervate prior to dilution compared to a composition that does contain coacervate prior to dilution.

1. Measurement of % Transmittance (% T) During Dilution

Coacervate formation upon dilution for a transparent or translucent composition can be assessed using a spectrophotometer to measure the percentage of light transmitted through the diluted sample (% T). As percent light transmittance (% T) values measured of the dilution decrease, typically higher levels of coacervate are formed. Dilutions samples at various weight ratios of water to composition can be prepared, for example 2 parts of water to 1 part composition (2:1), or 7.5 parts of water to 1 part composition (7.5:1), or 16 parts of water to 1 part composition (16:1), or 34 parts of water to 1 part composition (34:1), and the % T measured for each dilution ratio sample. Examples of possible dilution ratios may include 2:1, 3:1, 5:1, 7.5:1, 11:1, 16:1, 24:1, or 34:1. By averaging the % T values for samples that span a range of dilution ratios, it is possible to simulate and ascertain how much coacervate a composition on average would form as a consumer applies the composition to wet hair, lathers, and then rinses it out. Average % T can be calculated by taking the numerical average of individual % T measurements for the following dilution ratios: 2:1, 3:1, 5:1, 7.5:1, 11:1, 16:1, 24:1, and 34:1. Lower average % T indicates more coacervate is formed on average as a consumer applies the composition to wet hair, lathers and then rinses it out.

% T can be measured using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to insure no air bubbles are within the sample before the % T is measured by the spectrophotometer at 600 nm. Alternatively, multiple samples can be measured simultaneously by using a spectrophotometer such as the SpectraMax M-5 available from Molecular Devices. Multiple dilution samples can be prepared within a 96 well plate (VWR catalog #82006-448) and then transferred to a 96 well visible flat bottom plate (Greiner part #655-001), ensuring that no air bubbles are within the sample. The flat bottom plate is placed within the SpectraMax M-5 and % T measured using the Software Pro v.5™ software available from Molecular Devices.

2. Assessment of Coacervate Floc Size Upon Dilution

Coacervate floc size upon dilution can be assessed visually. Dilutions samples at various weight ratios of water to composition can be prepared, for example 2 parts of water to 1 part composition (2:1), or 7.5 parts of water to 1 part composition (7.5:1), or 16 parts of water to 1 part composition (16:1), or 34 parts of water to 1 part composition (34:1), and the % T measured for each dilution ratio sample. Examples of possible dilution ratios may include 2:1, 3:1, 5:1, 7.5:1, 11:1, 16:1, 24:1, or 34:1.

3. Wet Combing Force Method

Hair switches of 4 grams general population hair at 8 inches length are used for the measurement. Each hair switch is treated with 4 cycles (1 lather/rinse steps per cycle, 0.1 gm cleansing composition/gm hair on each lather/rinse step, drying between each cycle) with the cleansing composition. Four switches are treated with each shampoo. The hair is not dried after the last treatment cycle. While the hair is wet, the hair is pulled through the fine tooth half of two Beautician 3000 combs. Force to pull the hair switch through the combs is measured by a friction analyzer (such as Instron or MTS tensile measurement) with a load cell and outputted in gram-force (gf). The pull is repeated for a total of five pulls per switch. Average wet combing force is calculated by averaging the force measurement from the five pulls across the four hair switches treated with each cleansing composition. Data can be shown as average wet combing force through one or both of the two combs.

4. Deposition Method

Deposition of actives can be measured in vitro on hair tresses or in vivo on panelist's heads. The composition is dosed on a hair tress or panelist head at a controlled amount and washed according to a conventional washing protocol. For a hair tress, the tress can be sampled and tested by an appropriate analytical measure to determine quantity deposited of a given active. To measure deposition on a panelist's scalp, the hair is then parted on an area of the scalp to allow an open-ended glass cylinder to be held on the surface while an aliquot of an extraction solution is added and agitated prior to recovery and analytical determination of a given active. To measure deposition on a panelist's hair, a given amount of hair is sampled and then tested by an appropriate analytical measure to determine quantity deposited of a given active.

Cone/Plate Viscosity Measurement

The viscosities of the examples are measured by a Cone/Plate Controlled Stress Brookfield Rheometer R/S Plus, by Brookfield Engineering Laboratories, Stoughton, MA The cone used (Spindle C-75-1) has a diameter of 75 mm and 1° angle. The liquid viscosity is determined using a steady state flow experiment at constant shear rate of $2\ s^{-1}$ and at temperature of 26.7° C. The sample size is about 2.5 ml to about 3 ml and the total measurement reading time is 3 minutes.

Lather Characterization—Kruss DFA100 Lather Characterization

A cleansing composition dilution of 10 parts by weight water to 1 part by weight cleanser is prepared. The shampoo dilution is dispensed into the Kruss DFA100 which generates the lather and measures lather properties.

pH Method

First, calibrate the Mettler Toledo Seven Compact pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 4 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 7 buffer and press the calibrate button a second time. Wait until the pH icon stops flashing and press the calibrate button a third time. Rinse the electrode with distilled water and carefully wipe the electrode with a scientific cleaning wipe. Then submerse the electrode into the pH 10 buffer and press the calibrate button a third time. Wait until the pH icon stops flashing and press the measure button. Rinse the electrode with distilled water and carefully wipe with a scientific cleaning wipe. Submerse the electrode into the testing sample and press the read button. Wait until the pH icon stops flashing and record the value.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The following Examples illustrate various shampoo compositions. The Examples in Table 2 2 and Table 3 were prepared by conventional formulation and mixing techniques. The sclerotium gum was incorporated using high shear milling, as described herein.

The total sodium chloride in the examples in Table 2 and Table 3 was 0.07%. The total sodium chloride in the tables below was calculated based on the product specifications from the suppliers. The ratio of anionic to amphoteric surfactant in Table 2 and Table 3 3 was 0.9:1. The ratio of anionic surfactant to amphoteric surfactant is calculated by wt. %. The ratio of polymer charge density to inorganic salt in Table 2 and Table 3 was 18:1.

The ratio of polymer charge density to inorganic salt is the charge density of the polymer (meq/gm) to the wt. % of the inorganic salt, disregarding the units. If the composition contains more than one cationic polymer, then the ratio is calculated according to the polymer with the lowest charge density.

Figure 6B:
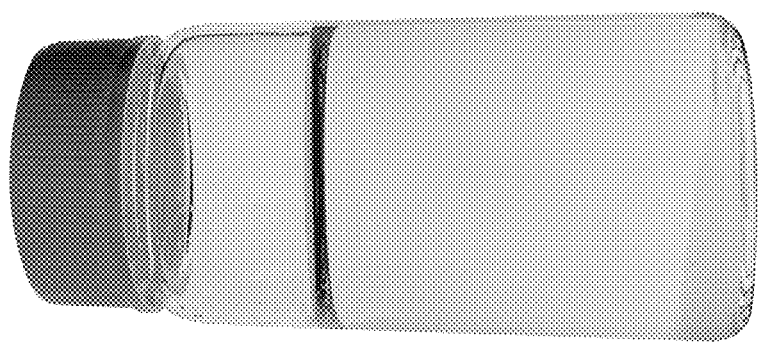
FIG. 6B is an image of Comparative Example C6.
Figure 6A:
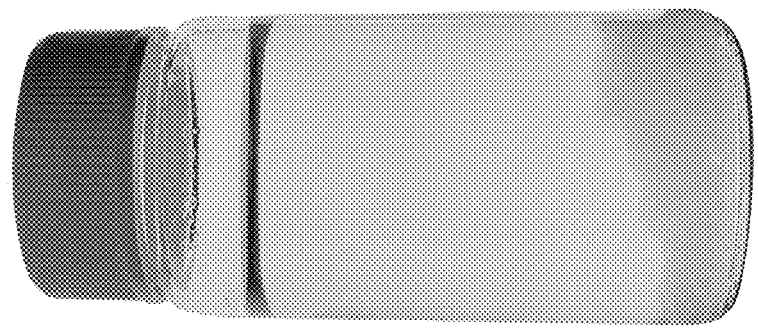
FIG. 6A is an image of Comparative Example C5.

For the examples and comparative examples Table 2 and Table 3, the phase stability was determined as follows. The examples were prepared and immediately put in a clear, glass jar of at least 1 inch width. The cap was screwed on the jar, finger tight. The example was stored at ambient temperatures (20-25° C.), away from direct sunlight, for 5 days. Then the composition was inspected to see if either haze and/or precipitate was visually detectable. The haze and/or precipitate can be suspended across the liquid shampoo composition or a portion thereof and/or at or near the bottom of the container. If either haze or precipitate were present, it was determined that the composition had multiple phases and was not phases stable. FIGS. 6A and 6B show Comparative Example C5 (containing 0.5% konjac gum thickener) and C6 (containing 0.5% gellan gum thickener), respectively. A precipitate can be seen towards the bottom of the container in both FIGS. 6A and 6B. If neither haze nor precipitate were present, it was determined that there was no in situ coacervate and the composition was a stable, single phase. It is believed that the stable shampoo examples would have improved product performance as compared to the examples that were not phase stable.

As used herein, "visually detect" or "visually detectable" means that a human viewer can visually discern the quality of the example with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of 1 meter.

The examples in Table 2 and Table 3, could also be formulated with silicones, opacifiers (e.g. glycol distearate, glycol stearate), non-silicone oils, micas, gums or anionic rheology modifiers and other ingredients that would cause the shampoo to have a hazy or hazier appearance. However, it is believed that adding these ingredients would not cause in situ coacervate to form or other phase instability prior to use.

TABLE 2

Comparative Shampoo Composition Examples

| Phase Stability | C1 One phase | C2 One phase | C3 Multiple phases | C4 Multiple phases | C5 Multiple phases | C6 Multiple phases |
|---|---|---|---|---|---|---|
| pH | 5.62 | 5.54 | 5.75 | 5.81 | 5.79 | 5.87 |
| Viscosity @ 2 s-1 (cps) | 2236 | 893 | 4846 | 8588 | 3896 | 3053 |
| Lauramidopropyl Betaine [1] | 9.75 | 9.75 | 9.75 | 9.75 | 9.75 | 9.75 |
| Sodium Cocoyl Isethionate [2] | 6.00 | 6.00 | 6.00 | 6.00 | 6.00 | 6.00 |
| Sodium Lauryl Sarcosinate [3] | 2.50 | 2.50 | 2.50 | 2.50 | 2.50 | 2.50 |
| Polyquaternium 10 [4] (JR-30M, CD 1.25 meq/g) | 0.55 | 0.25 | | 0.55 | 0.55 | 0.55 |
| Xanthan Gum [8] | | | 0.20 | 0.20 | | |
| Carrageenan [9] | | | 0.20 | 0.20 | | |
| Konjac Gum [10] | | | | | 0.50 | |
| Gellan Gum [11] | | | | | | 0.50 |
| Citric Acid [12] | To pH 5.5-6.1 | | | | | |
| Water, Preservatives, Perfume, and Optional Components | Q.S. to 100 | | | | | |

C1 and C2 in Table 2 were phase stable. However, neither example contains a thickener, and the viscosity is too low to be consumer preferred. It is suspected that these examples will be difficult to hold in a user's palm and apply across the hair.

C3-C6 contained an anionic thickener (e.g. xanthan gum, carrageenan, konjac gum, and gellan gum) separated into multiple phases, which is believed to not only impact the appearance of the product, but will also impact product performance Thus, C3-C6 will likely not be consumer preferred.

Yield stress was not measured for the examples in Table 2 because the examples were not consumer acceptable.

TABLE 3

Shampoo Composition Examples

| | Ex. 1 | Ex. 2 | Ex. 3 | Ex. 4 |
|---|---|---|---|---|
| Phase Stability | One phase | One phase | One phase | One phase |
| pH | 5.86 | 5.84 | 5.82 | 5.50 |
| Viscosity @ 2 s-1 (cps) | 4192 | 2681 | 4889 | 10615 |
| Yield Stress, Herschel-Bulkley @ shear rate $10^{-2}$ to $10^{-4}$ s$^{-1}$ (Pa) | 0.004 | 0.008 | 0.017 | 0.16 |
| Lauramidopropyl Betaine [1] | 9.75 | 9.75 | 9.75 | 9.75 |
| Sodium Cocoyl Isethionate [2] | 6.00 | 6.00 | 6.00 | 6.00 |
| Sodium Lauryl Sarcosinate [3] | 2.50 | 2.50 | 2.50 | 2.50 |
| Polyquaternium 10 [4] (JR-30M, CD 1.25 meq/g) | 0.55 | 0.55 | 0.55 | 0.55 |
| Sclerotium Gum [5,6] | 0.50 | 1.00 | | |
| Sclerotium Gum and Citrus Limon Peel Powder [7] | | | 0.50 | 1.00 |
| Citric Acid [12] | To pH 5.5-6.1 | | | |
| Water, Preservatives, Perfume, and Optional Components | Q.S. to 100 | Q.S. to 100 | Q.S. to 100 | Q.S. to 100 |

The Examples in

Table 3 were phase stable, have a pH that prevents the surfactant from hydrolyzing (e.g. greater than or equal to 5.5), and have a consumer acceptable viscosity (e.g. greater than or equal to 2700 Pa). It is believed that these examples would be consumer preferred, as compared to the comparative examples in Table 2.

The Examples in Table 4 and

Table 5 could be made and it is believed that these examples would be stable and have consumer acceptable viscosity. The Examples in Table 4 would have a total sodium chloride of 0.7% based on the specifications from suppliers and a ratio of polymer charge density to inorganic salt of 18:1.

TABLE 4

| | Ex. 5 | Ex. 6 | Ex. 7 |
|---|---|---|---|
| Lauramidopropyl Betaine [1] | 9.75 | 9.75 | 9.75 |
| Sodium Cocoyl Isethionate [2] | 6.00 | 6.00 | 6.00 |
| Sodium Lauryl Sarcosinate [3] | | | 4.00 |
| Polyquaternium 10 [4] (JR-30M, CD 1.25 meq/g) | 0.55 | 0.55 | 0.55 |
| Sclerotium Gum [5,6] | 0.50 | 0.50 | 0.50 |
| Sodium Benzoate [13] | 0.75 | 0.75 | 0.45 |
| Sodium Salicylate [14] | | 0.45 | 0.45 |
| Perfume | 1.00 | 1.00 | 1.00 |
| Citric Acid [12] | To pH 5.5-6.5 | | |
| Water | QS to 100 | QS to 100 | QS to 100 |
| Number of Ingredients | 8 | 9 | 10 |
| Ratio of Anionic to Amphoteric Surfactant | 0.6:1 | 0.6:1 | 1.0:1 |

TABLE 5

| | Ex. 8 | Ex. 9 | Ex. 10 | Ex. 11 | Ex. 12 | Ex. 13 | Ex. 14 |
|---|---|---|---|---|---|---|---|
| Lauramidopropyl Betaine [1] | 9.75 | 9.75 | | 5.36 | 2.44 | 2.44 | |
| Low Salt Cocamidopropyl Betaine [15] | | | 9.75 | | | | |
| Cocamidopropyl Betaine [16] | | | | 4.39 | 7.31 | 7.31 | 7.50 |
| Sodium Cocoyl Isethionate [2] | 6.00 | 6.00 | 6.00 | 6.00 | 6.00 | 6.00 | 4.50 |
| Sodium Lauryl Sarcosinate [3] | 2.50 | 2.50 | 2.50 | 2.50 | 2.50 | 2.50 | |

TABLE 5-continued

|  | Ex. 8 | Ex. 9 | Ex. 10 | Ex. 11 | Ex. 12 | Ex. 13 | Ex. 14 |
|---|---|---|---|---|---|---|---|
| Polyquaternium 10 [4] (JR-30M, CD 1.25 meq/g) | 0.55 | 0.55 | 0.55 | 0.55 |  |  |  |
| Polyquaternium 10 [19] (KG-30M, CD 1.9 meq/g) |  |  |  |  | 0.10 | 0.40 | 0.25 |
| Sclerotium Gum [5, 6] | 0.50 | 1.50 | 0.50 | 0.50 | 0.50 | 0.50 | 0.50 |
| Piroctone Olamine [17] | 0.50 |  |  |  |  |  |  |
| Zinc Pyrithione [18] |  | 1.00 |  |  |  |  |  |
| Water, Preservatives, pH adjusters, Perfume, and Optional Components | QS to 100 | QS to 100 | QS to 100 | QS to 100 | QS to 100 | QS to 100 | QS to 100 |
| Ratio of Anionic to Amphoteric Surfactant | 0.9:1 | 0.9:1 | 0.9:1 | 0.9:1 | 0.9:1 | 0.9:1 | 0.6:1 |
| Total Sodium Chloride (including from surfactant) | 0.07 | 0.07 | 0.06 | 0.81 | 1.3 | 1.3 | 1.3 |
| Ratio of Polymer Charge Density to Inorganic Salt | 18:1 | 18:1 | 21:1 | 1.5:1 | 1.5:1 | 1.5:1 | 1.5:1 |

Suppliers for Examples in Table 2 to Table 5
1. Mackam® DAB-ULS available from Solvay®. Specification Range: Solids=34-36%, Sodium Chloride=0-0.5%. Average values are used for calculations: Actives=35%, Sodium Chloride=0.25%.
2. Hostapon® SCI-85 C available from Clariant®
3. SP Crodasinic™ LS30/NP MBAL available from Croda®
4. UCARE™ Polymer JR-30M available from Dow®
5. Sclerotium Gum, Amigum ER available from Alban Muller®
6. Sclerotium Gum, Actigum® CS 11 QD available from Cargill®
7. Sclerotium Gum and Citrus Limon Peel Powder, Fiber Design Sensation® available from Cargill®
8. Xanthan Gum, Keltrol® CG-SFT available from CP Kelco®
9. Carrageenan, GENUVISCO® Carrageenan CG-131 available from CP Kelco®
10. Konjac Gum, Nutricol® XP 3464 available from FMC Corporation
11. Gellan Gum, Kelcogel® CG-LA available from CP Kelco®
12. Citric Acid USP Anhydrous Fine Granular available from ADM®
13. Sodium Benzoate available from Kalama®
14. Sodium Salicylate available from JQC (Huayin) Pharmaceutical Co., Ltd
15. Dehyton® PK 45 from BASF® with Sodium Chloride removed, resulting in 33.05% Dry Residue, 0.21% Sodium Chloride, 32.84% Active used for calculations.
16. TEGO® Betain CK PH 12 available from Evonik®. Specification Range: Actives=28-32%, Sodium Chloride=4.5-6%. Average values are used for calculations: Actives=30%, Sodium Chloride=5.25%.
17. Octopirox® available from Clariant®
18. Zinc Pyrithione available from Lonza®
19. UCARE™ Polymer KG-30M available from Dow®

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A phase-stable shampoo composition comprising:
  a) a surfactant system comprising:
    (i) about 3% to about 35% of an anionic surfactant comprising sodium, ammonium or potassium salts of isethionates, sodium, ammonium or potassium salts of sarcosinates, or a combination thereof;
    (ii) about 5% to about 15% of an amphoteric surfactant comprising a betaine, wherein the surfactant system is substantially free of sulfated surfactants;
  b) about 0.01% to about 2% of a cationic polymer comprising polyquaternium-10; and
  c) about 0.15% to about 1.5% of a thickener comprising sclerotium gum, wherein the composition has a viscosity of greater than 2500 cP and a pH of greater than 5.5.
2. The phase-stable shampoo composition of claim 1, further comprising less than about 1% inorganic salt.
3. The phase-stable shampoo composition of claim 2, wherein the inorganic salt is selected from sodium chloride, potassium chloride, sodium sulfate, ammonium chloride, sodium bromide, and combinations thereof.
4. The phase-stable shampoo composition of claim 1, wherein the phase-stable shampoo composition has a viscosity of greater than 4000 cP.
5. The phase-stable shampoo composition of claim 1, wherein the phase-stable shampoo composition has a pH greater than 5.7.
6. The phase-stable shampoo composition of claim 1, wherein the phase-stable shampoo composition has a yield stress of greater than 0.003 Pa at a shear rate 10-2 to 10-4 s-1 according to the Herschel-Bulkley model.

7. The phase-stable shampoo composition of claim 1, wherein the phase-stable shampoo composition has a ratio of polymer charge density to total inorganic salt of greater than or equal to 1.2:1.

8. The phase-stable shampoo composition of claim 1, wherein the phase-stable shampoo composition is substantially free of alkyl polyglucoside.

9. The phase-stable shampoo composition of claim 1, wherein the phase-stable shampoo composition is substantially free of fatty esters.

10. The phase-stable shampoo composition of claim 1, wherein the phase-stable shampoo composition has a percent transparency % T at 600 nm of greater than 70%.

11. The phase-stable shampoo composition of claim 1, wherein the phase-stable shampoo composition lacks an in situ coacervate, as determined by the Microscopy Method to Determine Lack of In Situ Coacervate.

12. The phase-stable shampoo composition of claim 1, further comprising an antidandruff agent.

13. The phase-stable shampoo composition of claim 12, wherein the antidandruff agent is selected from piroctone olamine, zinc pyrithione, and combinations thereof.

14. The phase-stable shampoo composition of claim 1, wherein the phase-stable shampoo composition is substantially free of silicones.

15. The phase-stable shampoo composition of claim 1, wherein the composition has 9 or fewer ingredients.

16. A method of making the phase-stable shampoo composition of claim 1, wherein the sclerotium gum is added using high shear milling.

* * * * *